US010383651B2

(12) United States Patent
Pell et al.

(10) Patent No.: US 10,383,651 B2
(45) Date of Patent: Aug. 20, 2019

(54) INSTRUMENTS, DEVICES, AND RELATED METHODS FOR SOFT TISSUE DISSECTION

(71) Applicant: PHYSCIENT, INC., Durham, NC (US)

(72) Inventors: Charles A. Pell, Durham, NC (US); Hugh C. Crenshaw, Durham, NC (US)

(73) Assignee: Physcient, Inc., Durham, NC (US)

(*) Notice: Subject to any disclaimer, the term of this patent is extended or adjusted under 35 U.S.C. 154(b) by 232 days.

(21) Appl. No.: 15/304,720

(22) PCT Filed: Apr. 22, 2015

(86) PCT No.: PCT/US2015/027156
§ 371 (c)(1),
(2) Date: Oct. 17, 2016

(87) PCT Pub. No.: WO2015/164536
PCT Pub. Date: Oct. 29, 2015

(65) Prior Publication Data
US 2017/0035449 A1    Feb. 9, 2017

Related U.S. Application Data

(60) Provisional application No. 61/982,633, filed on Apr. 22, 2014.

(51) Int. Cl.
*A61B 17/32*    (2006.01)
(52) U.S. Cl.
CPC ........... *A61B 17/32002* (2013.01); *A61B 2017/32006* (2013.01); *A61B 2017/320028* (2013.01); *A61B 2017/320044* (2013.01)

(58) Field of Classification Search
CPC ....... A61B 2017/320028; A61B 2017/320044; A61B 2017/320032; A61B 2017/32006;
(Continued)

(56) References Cited

U.S. PATENT DOCUMENTS 900,300 A    10/1908    Nicolas
1,192,451 A    7/1916    Pfefferkorn
(Continued)

FOREIGN PATENT DOCUMENTS

CN    101686839 A    3/2010
CN    103648415 A    3/2014
(Continued)

OTHER PUBLICATIONS

U.S. Appl. No. 13/872,766., filed Apr. 29, 2013.
(Continued)

*Primary Examiner* — Katrina M Stransky
(74) *Attorney, Agent, or Firm* — Withrow & Terranova, P.L.L.C.

(57) ABSTRACT

A differential dissecting instrument for differentially dissecting complex tissue comprising is disclosed. The differential dissecting instrument comprises a rotary drive train having a central, longitudinal axis, a distal end, and a proximal end. The differential dissecting instrument also comprises at least one differential dissecting bluntwheel, wherein the at least one differential dissecting bluntwheel is rotatably associated with the distal end of the rotary drive train, has at least one axis of rotation substantially transverse to the central, longitudinal axis of the rotary drive train, and is rotated by the rotary drive train. The bluntwheel may comprise projections that are configured to differentially dissect a complex tissue when the differential dissecting instrument is in operation.

10 Claims, 14 Drawing Sheets

(58) Field of Classification Search
CPC .. A61B 2017/320004; A61B 17/320016; A61B 2017/00314; A61B 17/32002; A61B 2017/00398
See application file for complete search history.

(56) References Cited

U.S. PATENT DOCUMENTS

| | | | |
|---|---|---|---|
| 1,506,510 A | 8/1924 | Thuau | |
| 1,945,247 A | 1/1934 | Wezel | |
| 2,547,134 A | 4/1951 | McLean | |
| 2,766,524 A | 10/1956 | Dagneau | |
| 2,972,350 A | 2/1961 | Deker | |
| 3,263,681 A | 8/1966 | Nechtow et al. | |
| 3,435,522 A | 4/1969 | Wezel et al. | |
| 3,554,197 A | 1/1971 | Dobble | |
| 3,618,611 A | 11/1971 | Urban | |
| 3,978,862 A | 9/1976 | Morrison | |
| 4,106,181 A | 8/1978 | Mattchen | |
| 4,432,117 A | 2/1984 | Iskiw | |
| 4,477,256 A | 10/1984 | Hirsch | |
| 4,490,885 A | 1/1985 | Iskiw et al. | |
| 4,572,187 A | 2/1986 | Schetrumpf | |
| 4,608,982 A | 9/1986 | Pollard | |
| 4,749,376 A | 6/1988 | Kensey et al. | |
| 4,768,504 A | 9/1988 | Ender | |
| 4,844,088 A | 7/1989 | Kambin | |
| 4,990,134 A | 2/1991 | Auth | |
| 5,201,752 A | 4/1993 | Brown et al. | |
| 5,205,816 A | 4/1993 | Dodson et al. | |
| 5,405,348 A | 4/1995 | Anspach, Jr. et al. | |
| 5,441,445 A | 8/1995 | Karubian et al. | |
| 5,445,561 A | 8/1995 | Elmer | |
| 5,456,011 A | 10/1995 | Inkster | |
| 5,522,788 A | 6/1996 | Kuzmak | |
| 5,527,331 A | 6/1996 | Kresch et al. | |
| 5,591,186 A | 1/1997 | Wurster et al. | |
| 5,658,307 A | 8/1997 | Exconde | |
| 5,707,383 A | 1/1998 | Bays et al. | |
| 5,725,479 A | 3/1998 | Knight et al. | |
| 5,779,713 A | 7/1998 | Turjanski et al. | |
| 5,817,121 A | 10/1998 | Christoudias | |
| 5,871,497 A | 2/1999 | Young | |
| 5,919,203 A | 7/1999 | Husted et al. | |
| 5,925,055 A | 7/1999 | Adrian et al. | |
| 6,001,120 A | 12/1999 | Levin | |
| 6,080,102 A | 6/2000 | Konou et al. | |
| 6,391,040 B1 | 5/2002 | Christoudias | |
| 6,423,078 B1 | 7/2002 | Bays et al. | |
| 6,869,439 B2 | 3/2005 | White et al. | |
| 7,367,981 B2 | 5/2008 | Bernaz | |
| 7,422,592 B2 | 9/2008 | Morley et al. | |
| D581,053 S | 11/2008 | Gesler, III | |
| 7,540,875 B2 | 6/2009 | Jessen | |
| 7,686,823 B2 | 3/2010 | Pingleton et al. | |
| 7,842,058 B2 | 11/2010 | Simpson et al. | |
| 8,048,100 B2 | 11/2011 | Kadykowski et al. | |
| 8,052,662 B2 | 11/2011 | Zelickson et al. | |
| 8,157,832 B2 | 4/2012 | Refai | |
| 8,372,096 B2 | 2/2013 | Kadykowski et al. | |
| 8,460,331 B2 | 6/2013 | Chin | |
| 8,636,759 B2 | 1/2014 | Pingleton et al. | |
| 2003/0009166 A1 | 1/2003 | Moutafis et al. | |
| 2003/0144680 A1 | 7/2003 | Kellogg et al. | |
| 2005/0107816 A1 | 5/2005 | Pingleton et al. | |
| 2005/0209610 A1 | 9/2005 | Carrison | |
| 2006/0009796 A1 | 1/2006 | Carusillo et al. | |
| 2007/0167966 A1 | 7/2007 | Simpson et al. | |
| 2008/0119860 A1 | 5/2008 | McCarthy | |
| 2008/0306335 A1 | 12/2008 | Lau et al. | |
| 2009/0261690 A1 | 10/2009 | Mashimo et al. | |
| 2009/0312783 A1 | 12/2009 | Whayne et al. | |
| 2010/0010525 A1 | 1/2010 | Lockard et al. | |
| 2010/0016853 A1 | 1/2010 | Burbank | |
| 2010/0114138 A1 | 5/2010 | Graham | |
| 2010/0222801 A1 | 9/2010 | Pingleton et al. | |
| 2010/0256662 A1 | 10/2010 | Racenet et al. | |
| 2010/0312186 A1 | 12/2010 | Suchdev et al. | |
| 2011/0034918 A1 | 2/2011 | Reschke | |
| 2012/0071909 A1 | 3/2012 | Fischvogt et al. | |
| 2012/0101489 A1 | 4/2012 | Bloom et al. | |
| 2012/0109172 A1 | 5/2012 | Schmitz et al. | |
| 2012/0191121 A1* | 7/2012 | Chen | A61B 10/0266 606/180 |
| 2012/0209141 A1* | 8/2012 | Peliks | A61B 10/0266 600/564 |
| 2013/0310869 A1 | 11/2013 | Crenshaw et al. | |
| 2013/0331833 A1 | 12/2013 | Bloom | |
| 2014/0058394 A1* | 2/2014 | Siegal | A61B 17/1671 606/80 |
| 2014/0114339 A1 | 4/2014 | Pingleton et al. | |
| 2014/0364890 A1 | 12/2014 | Moody et al. | |

FOREIGN PATENT DOCUMENTS

| | | |
|---|---|---|
| EP | 1882538 A2 | 1/2008 |
| EP | 2777523 A1 | 9/2014 |
| WO | 0149194 A2 | 7/2001 |
| WO | 2006017066 A2 | 2/2006 |
| WO | 2007100914 A2 | 9/2007 |
| WO | 2008022257 A2 | 2/2008 |
| WO | 2008127887 A1 | 10/2008 |

OTHER PUBLICATIONS

U.S. Appl. No. 14/065,191, filed Oct. 28, 2013.
U.S. Appl. No. 13/304,670, filed Oct. 17, 2016.
Notice of Allowance and Examiner-Initiated Interview Summary for U.S. Appl. No. 14/065,191, dated Jan. 10, 2017, 11 pages.
First Office Action for Chinese Patent Application No. 201480071443.8, dated Nov. 29, 2017, 27 pages.
Extended European Search Report for European Patent Application No. 17180994.0, dated Dec. 6, 2017, 8 pages.
Examiner's Decision of Rejection for Japanese Patent Application No. 2015-509216, dated Dec. 19, 2017, 8 pages.
Further Examination Report for New Zealand Patent Application No. 725053, dated Jan. 8, 2018, 2 pages.
Notice of Eligibility for Grant and Supplementary Examination Report for Singapore Patent Application No. 11201603273P, dated Sep. 4, 2017, 3 pages.
Extended European Search Report for European Patent Application No. 15780427.9, dated Nov. 14, 2017, 7 pages.
Examination Report No. 1 for Australian Patent Application No. 2013251330, dated Jun. 22, 2017, 5 pages.
Third Office Action for Chinese Patent Application No. 201380034142.3, dated Sep. 5, 2017, 4 pages.
Examination Report No. 2 for Australian Patent Application No. 2013251330, dated Jun. 4, 2018, 2 pages.
Notice of Acceptance for Australian Patent Application No. 2013251330, dated Jul. 2, 2018, 3 pages.
Examination Report No. 1 for Australian Patent Application No. 2014342631, dated Jul. 27, 2018, 3 pages.
Extended European Search Report for European Patent Application No. 14857187.0, dated Jun. 12, 2017, 8 pages.
First Examination Report for New Zealand Patent Application No. 725053, dated May 3, 2017, 5 pages.
Second Office Action and Search Report for Chinese Patent Application No. 201380034142.3, dated Feb. 15, 2017, 21 pages.
Notice of Rejection for Japanese Patent Application No. 2015-509216, dated Feb. 28, 2017, 18 pages.
Supplementary Examination Report for Singapore Patent Application No. 11201406985P, dated Jan. 19, 2017, 2 pages.
International Preliminary Report on Patentability for International Patent Application No. PCT/US2013/038673, dated Nov. 6, 2014, 16 pages.
Cox, III, et al., "Decreased Splatter in Dermabrasion," Archives of Facial Plastic Surgery, vol. 2, Jan.-Mar. 2000, pp. 23-26.
Non-Final Office Action for U.S. Appl. No. 13/872,766, dated Jun. 17, 2016, 34 pages.

(56) References Cited

OTHER PUBLICATIONS

Non-Final Office Action for U.S. Appl. No. 14/065,191, dated May 31, 2016, 23 pages.
First Office Action for Chinese Patent Application No. 201380034142.3, dated Jun. 2, 2016, 8 pages.
Extended European Search Report for European Patent Application No. 13780834.1, dated Aug. 21, 2015, 5 pages.
Examination Report for European Patent Application No. 13780834.1, dated Jul. 21, 2016, 3 pages.
First Examination Report for New Zealand Patent Application No. 701634, dated Jan. 14, 2016, 3 pages.
Further Examination Report for New Zealand Patent Application No. 701634, dated Apr. 26, 2016, 2 pages.
Further Examination Report Postponed Acceptance for New Zealand Patent Application No. 701634, dated Jul. 27, 2016, 1 page.
International Search Report and Written Opinion for PCT/US2013/038673 dated Sep. 27, 2013, 23 pages.
International Search Report and Written Opinion for PCT/US2014/062382, dated Feb. 3, 2015, 12 pages.
International Preliminary Report on Patentability for PCT/US2014/062382, dated May 12, 2016, 9 pages.
Invitation to Pay Additional Fees and Partial International Search for PCT/US2015/026466, dated Jun. 18, 2015, 7 pages.
International Search Report and Written Opinion for International Patent Application No. PCT/US2015/026466, dated Sep. 15, 2015, 14 pages.
International Preliminary Report on Patentability for International Patent Application No. PCT/US2015/026466, dated Oct. 27, 2016, 9 pages.
International Search Report and Written Opinion for PCT/US2015/027156, dated Aug. 3, 2015, 11 pages.
International Preliminary Report on Patentability for International Patent Application No. PCT/US2015/027156, dated Nov. 3, 2016, 9 pages.
Notice of Allowance and Examiner-Initiated Interview Summary for U.S. Appl. No. 13/872,766, dated Nov. 4, 2016, 11 pages.
Notice of Rejection for Japanese Patent Application No. 2016-526849, dated Jul. 31, 2018, 12 pages.
Non-Final Office Action for U.S. Appl. No. 15/304,679, dated Feb. 4, 2019, 11 pages.
Second Office Action for Chinese Patent Application No. 201480071443.8, dated Oct. 12, 2018, 12 pages.
Examination Report for European Patent Application No. 14857187.0, dated Jan. 31, 2019, 6 pages.
Final Notice of Rejection for Japanese Patent Application No. 2016-526849, dated Jan. 22, 2019, 9 pages.
Notice of Rejection for Japanese Patent Application No. 2016-563016, dated Feb. 12, 2019, 11 pages.
First Office Action for Mexican Patent Application No. MX/a/2014/013035, dated Feb. 11, 2019, 4 pages.
Office Action for Canadian Patent Application No. 2,871,827, dated May 3, 2019, 3 pages.
Non-Final Office Action for U.S. Appl. No. 15/457,169, dated Apr. 26, 2019, 26 pages.

* cited by examiner

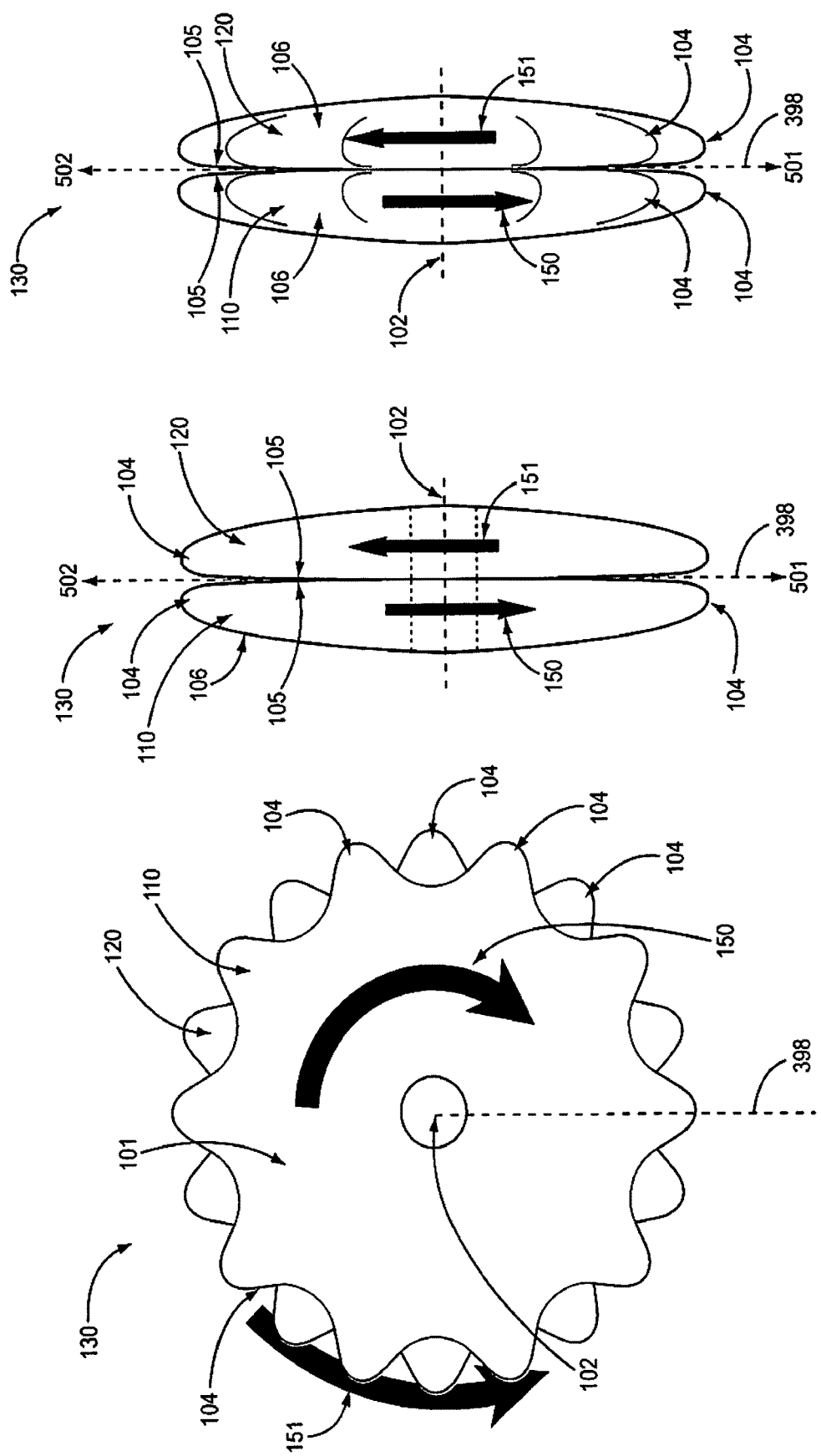

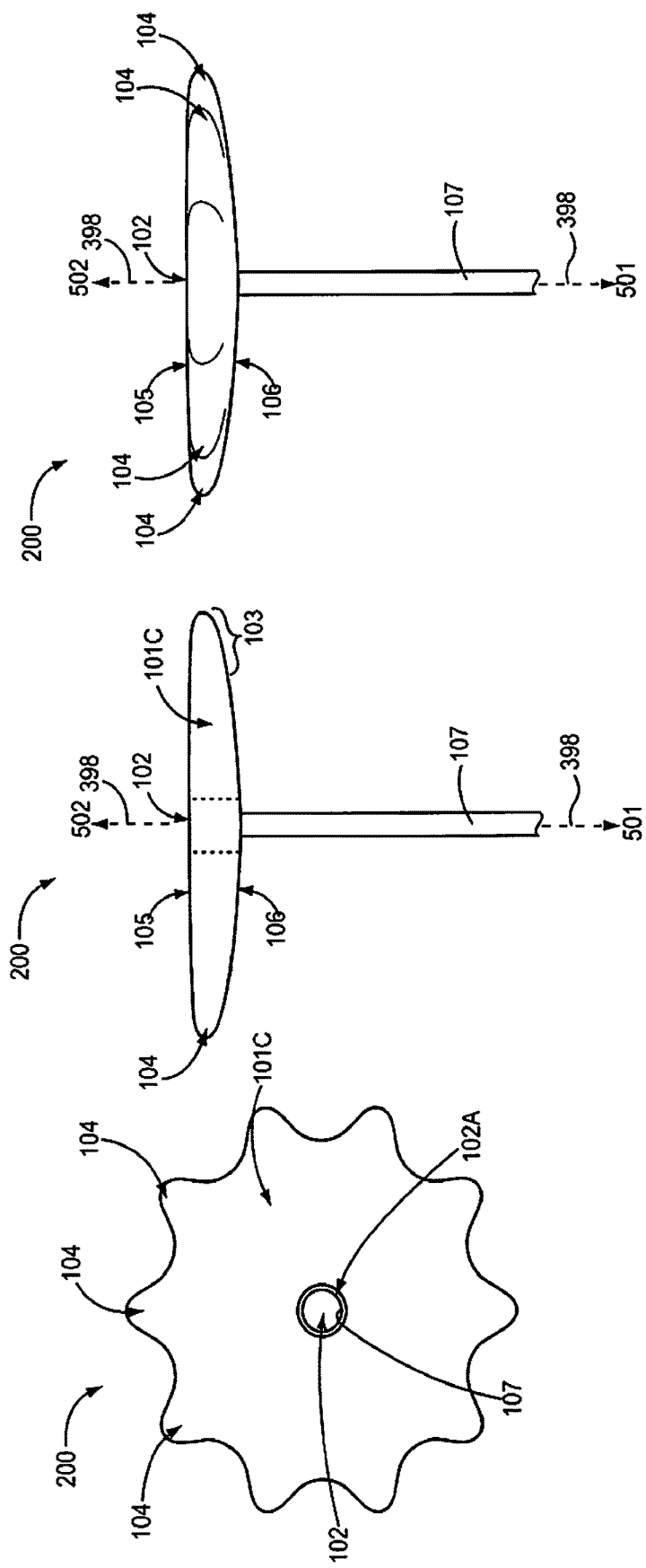

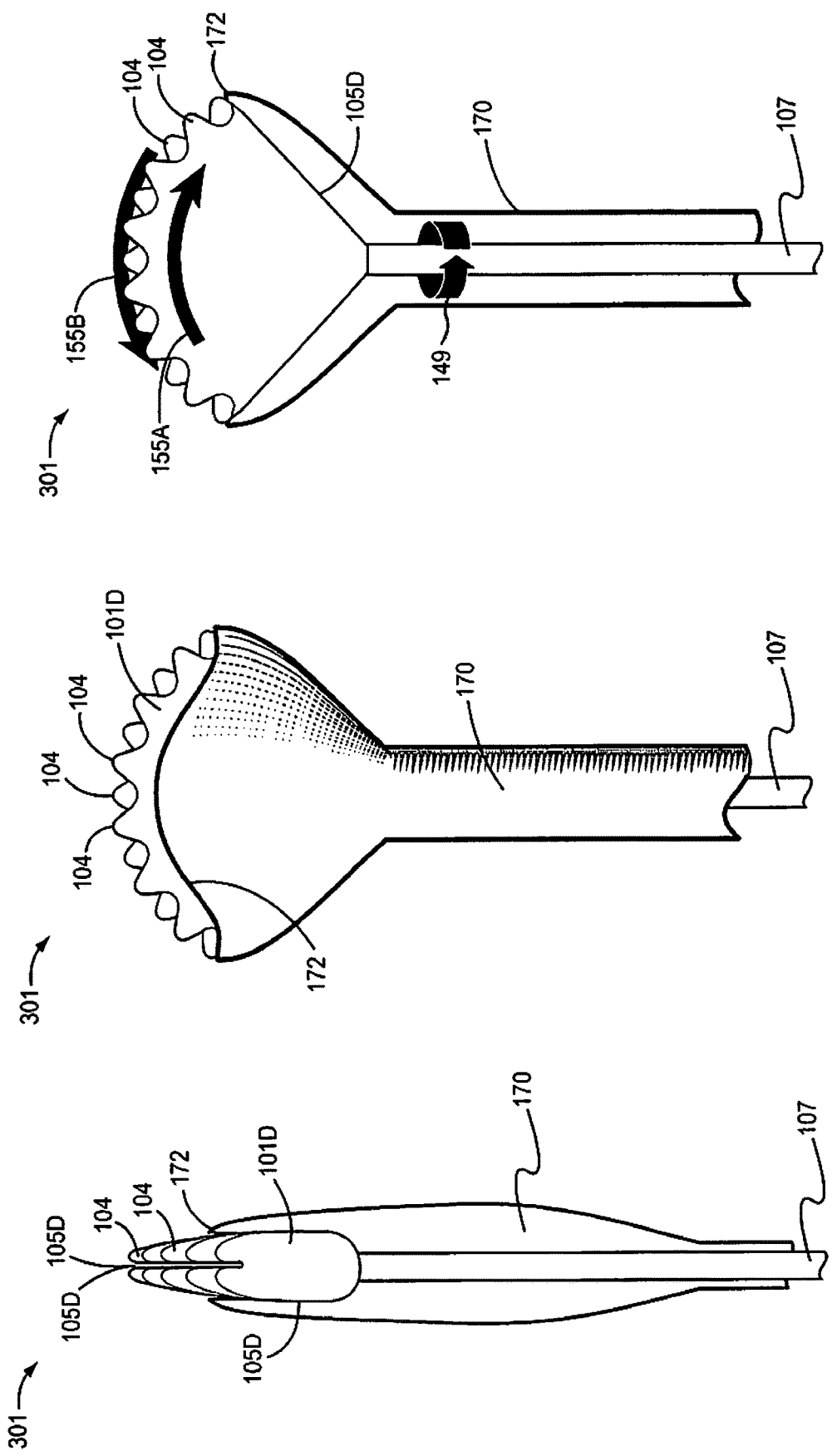

INSTRUMENTS, DEVICES, AND RELATED METHODS FOR SOFT TISSUE DISSECTION

This application is a 35 U.S.C. § 371 national phase filing of International Application No. PCT/US2015/027156, filed Apr. 22, 2015, the disclosure of which is incorporated herein by reference in its entirety.

PRIORITY APPLICATIONS

The present application claims priority to U.S. Provisional Patent Application No. 61/982,633 entitled "Instruments, Devices, and Related Methods for Soft Tissue Dissection," filed on Apr. 22, 2014, which is incorporated herein by reference in its entirety.

The present application is also related to co-pending U.S. patent application Ser. No. 14/065,191, entitled "Instruments, Devices, and Related Methods for Soft Tissue Dissection," filed on Oct. 28, 2013, now issued as U.S. Pat. No. 9,592,069, which in turn is a continuation-in-part application of, and claims priority to, co-pending U.S. patent application Ser. No. 13/872,766 entitled "Instruments, Devices, and Related Methods for Soft Tissue Dissection," filed Apr. 29, 2013, now issued as U.S. Pat. No. 9,538,995, which in turn claims priority to the following three Provisional applications: U.S. Provisional Patent Application No. 61/783,834, entitled "Instruments, Devices, and Related Methods for Soft Tissue Dissection," filed on Mar. 14, 2013; U.S. Provisional Patent Application No. 61/744,936, entitled "Instrument for Soft Tissue Dissection," filed on Oct. 6, 2012; and U.S. Provisional Patent Application No. 61/687,587, entitled "Instrument for Soft Tissue Dissection," filed on Apr. 28, 2012, all of which are incorporated herein by reference in their entireties.

The present application is also related to PCT Patent Application No. PCT/US15/26466, entitled "Methods and Devices for Soft Tissue Dissection," filed on Apr. 17, 2015, which in turn claims priority to U.S. Provisional Patent Application No. 61/981,556, entitled "Methods and Devices for Soft tissue Dissection," filed on Apr. 18, 2014, both of which are incorporated herein by reference in their entireties.

BACKGROUND

Field of the Disclosure

The field of the disclosure relates to methods or devices used to dissect tissue during surgery or other medical procedures.

Technical Background

Surgeons sever or separate patients' tissues as a major component of most surgical procedures. Called "dissection," this is how surgeons tunnel from an accessible region of a patient to reach a target within. The two dominant dissection techniques are: (1) "sharp dissection," where surgeons sever tissues with either scissors, scalpels, electrosurgical devices, and other cutting instruments; and (2) "blunt dissection," consisting of separating tissues by controlled tearing of one tissue from another.

The advantage of sharp dissection is that the cutting instrument easily cuts through any tissue. The cut itself is indiscriminate, slicing through all tissues to which the instrument is applied. This is also the disadvantage of sharp dissection, especially when trying to isolate a first tissue without damaging it, when the first tissue is embedded in, and is obscured by, a second tissue, or more commonly, is enveloped in many tissues. Accidental cutting of a blood vessel, a nerve, or bowel, for example, is a constant threat for even the most experienced surgeons and can rapidly lead to serious, even life-threatening, intra-operative complications, with prolonged consequences for the patient. When employing minimally invasive procedures, for example laparoscopy or the use of a surgical robot, the chances of surgical error increase.

Isolation of a first tissue embedded in other tissues is therefore frequently performed by blunt dissection. In blunt dissection, a blunt instrument is used to force through a tissue, to force apart two tissues, or to otherwise separate tissues by tearing rather than cutting. Almost all surgeries require blunt dissection of tissues to expose target structures, such as blood vessels to be ligated, or nerve bundles to be avoided. Examples in thoracic surgery include isolation of blood vessels during hilar dissection for lobectomy and exposure of lymph nodes. In plastic surgery, blunt dissection comprises the lion's share of many procedures, consisting of undermining very large areas of the patient's skin, where poor blunt dissection can result in hematomas, dermal punctures, and necrosis of the skin.

Blunt dissection includes a range of maneuvers, including various ways to tease apart or tear soft tissues, such as the insertion of blunt probes or instruments, inverted action (i.e., spreading) of forceps, and pulling of tissues with forceps or by rubbing with a "swab dissector" (e.g., surgical gauze held in a forceps, or a purpose-built, disposable swab stick such as a Kitner). When needed, sharp dissection is used judiciously to cut tissues that resist tearing during blunt dissection.

The general goal of blunt dissection is to tear or otherwise disrupt occluding tissue, such as membranes and mesenteries, away from the target structure without tearing or disrupting either the target structure or critical structures such as nearby vessels or nerves. The surgeon capitalizes on the different mechanical behaviors of tissues, such as the different stiffness of adjacent tissues, or the existence of planes of softer tissue between firmer tissues. Frequently, the surgeon's goal is to isolate a target tissue that is mechanically firm, being composed of more tightly packed fibrous components, and is embedded in a tissue that is mechanically soft, being composed of more loosely packed fibrous components (for example, loose networks of collagen, reticulin, or elastin). More tightly packed fibrous tissues include tissues composed of tightly packed collagen and other fibrous connective tissues, usually having highly organized anisotropic distributions of fibrous components, often with hierarchical composition. Examples include blood vessels, nerve sheaths, muscles, fascia, bladders, and tendons. More loosely packed fibrous tissues have a much lower number of fibers per unit volume or are composed of less well organized materials such as fat and mesenteries. Fibrous components include fibers, fibrils, filaments, and other filamentous components. When a tissue is referred to as "fibrous", the reference is typically to extracellular filamentous components, such as collagen and elastin—proteins that polymerize into linear structures of varying and diverse complexity to form the extracellular matrix. As mentioned in the previous paragraph, the density, orientation, and organization of fibrous components greatly determine the tissue's mechanical behavior. Sometimes, tissues are referred to as "tough, fibrous tissues" indicating that the fibrous or filamentous components are densely packed, organized, and comprise a significant fraction of the bulk of the tissue. However, all tissues are fibrous, to one extent or another, with fibers and other filamentous extracellular components being present in virtually every tissue.

What is important to the present discussion is that softer tissues tear more easily than firmer tissues, so blunt dissection attempts to proceed by exerting sufficient force to tear softer tissue but not firmer tissue.

Blunt dissection can be difficult, tedious, dangerous, and is often time-consuming. Judging the force to tear a soft tissue, but not a closely apposed firm tissue, is not easy. Thus, blood vessels can be torn. Nerves can be stretched or torn. In response, surgeons attempt judicious sharp dissection, but blood vessels, nerves, and airways can be cut, especially the smaller side branches, which become exponentially more common at smaller scales. This all leads to long, tedious dissections and increased risk of complications, like bleeding, air leaks from the lungs, and nerve damage. Complications of blunt dissection are common, as are repairs.

Surgeons frequently use forceps for blunt dissection. Forceps include finger engagers, a pivot, and two jaws for clamping together on tissues, but surgeons often employ forceps in a spreading mode, forcing the jaws apart in an attempt to tear or rend two adjacent tissues apart. This secondary use of forceps is common, but forceps are far from ideal for blunt dissection.

Laparoscopic and thoracoscopic (collectively referred here as "endoscopic") instruments use a similar action, albeit at the distal end of a very long shaft piercing the patient's body wall through a trocar. This arrangement imposes even more challenges, making laparoscopic blunt dissection more difficult, lengthening the time of procedures, and increasing the chances of intraoperative complications.

For either instrument, forceps 10 or endoscopic forceps 10, a surgeon performs blunt dissection by closing the forceps, pushing the closed forceps into a tissue and then, optionally, opening the forceps inside the tissue, using the force applied by opening of the jaws of the forceps to tear the tissue apart. A surgeon thus proceeds to dissect a tissue by a combination of pushing into the tissue and opening the jaws of the forceps.

Blunt dissection is commonly used for wet and slick tissues, and the smooth, passive surfaces of most surgical instruments slide easily along the tissue, impairing the instrument's ability to gain purchase and separate the tissue. Furthermore, the surgeon has only limited control, being able only to jab, move sideways, or separate. An improved instrument for blunt dissection that could differentially separate soft tissues while not disrupting firm tissues would greatly facilitate many surgeries. Of further utility would be an improved instrument that was as simple as possible, getting the job done with as few moving parts as can be achieved, whilst increasing both safety and speed.

SUMMARY OF THE DETAILED DESCRIPTION

Embodiments disclosed herein include methods and devices for blunt dissection, which differentially disrupt soft tissues while not disrupting firm tissues. In particular, in one embodiment, components for simplified tissue engaging surfaces and a drive mechanism for a powered differential dissecting instrument for differentially dissecting complex tissue are disclosed. The differential dissection instrument may be handheld, or may form a portion of a surgical machine, such as a laparoscopic instrument or a teleoperated surgical robot.

In one embodiment, a differential dissecting instrument for differentially dissecting complex tissue comprising is disclosed. The differential dissecting instrument comprises a rotary drive train having a central, longitudinal axis, a distal end, and a proximal end. The differential dissecting instrument also comprises at least one differential dissecting bluntwheel, wherein the at least one differential dissecting bluntwheel is rotatably associated with the distal end of the rotary drive train, has at least one axis of rotation substantially transverse to the central, longitudinal axis of the rotary drive train, and is rotated by the rotary drive train. The bluntwheel may comprise projections that are configured to differentially dissect a complex tissue when the differential dissecting instrument is in operation.

In another embodiment, the tissue-engaging surfaces disclosed herein comprise two sets of blunt, differentially dissecting, tissue-engaging projections configured to pass one another in close approximation and in opposite directions. The tissue to be differentially dissected can be presented with these twin sets of tissue engaging projections via opposed linear motions or opposed rotational motions, in a concentrated point or along an edge, or by a self-supporting set of tissue engaging projections, or by an exposed portion of tissue engaging projections otherwise covered by a shroud or housing. The two sets of passing projections to be presented to a complex tissue might be achieved by locating a linear series of the blunt, differentially dissecting, tissue-engaging projections along an edge of an object, for example along a pair of rods, bars, or other linear forms possessing an edge, or, if continuous cyclic passage of the blunt, differentially dissecting, tissue-engaging projections is desired, a pair of belts. As it is desirable to keep a surgical instrument small and simple, it is advantageous to locate the blunt, differentially dissecting, tissue-engaging projections along the edge of, or form the edge of, a small wheel, disk, or other rotatable form. Hereinafter, a wheel or disk that sports blunt, differentially dissecting, tissue-engaging projections along or forming its edge or margin is referred to as a "bluntwheel."

One embodiment of the distal-most, tissue-contacting tip of a differential dissection instrument may comprise two such bluntwheels. The bluntwheels may be roughly planar, situated parallel to one another, and coaxially rotatable about a common axis transverse to, or at least not parallel to, a long axis of the surgical instrument. The bluntwheels may also be substantially apposed or even in contact, such that when the first wheel is rotated clockwise about the common axis while simultaneously the second wheel is rotated counterclockwise, the twin sets of blunt, differentially dissecting, tissue-engaging projections pass closely in opposing directions, thus differentially dissecting a complex tissue. The bluntwheels herein can be constructed of a high-modulus material, like steel, or PEEK, having a Young's modulus greater than one gigapascal. Alternatively, the bluntwheels can be made of a polymeric elastomer, like a polyurethane, and possess a Young's modulus of less than one megapascal, depending on the surgical procedure involved, the type of tissue to be dissected, or the relative dimensions of the surgical instrument and the anatomical structure of interest.

Another embodiment of the distal-most, tissue-contacting tip of a differential dissection instrument may include a flexible bluntwheel. The tip may comprise one roughly planar, flexible, deformable, elastic bluntwheel rotatable about an axis, where the axis can be coaxial and coincident with a driveshaft upon which the bluntwheel is firmly affixed. Further, the differential dissecting instrument may be configured to spin the driveshaft (and thus the associated flexible bluntwheel) while intentionally interfering with the free rotation in space of the edge of, margin of, outer limb of, or similar substantial portions of the roughly planar, natural disk or wheel-like form of the flexible, deformable, elastic bluntwheel.

In one embodiment, of the device is configured so that, in operation, the edge or margin of the freely spinning flexible, deformable, elastic bluntwheel is impinged upon, distorted, deformed, flexed, folded, stressed, strained, re-directed, bent, or otherwise driven out of its unstressed, roughly planar, disk-like state by another portion of the differential dissecting instrument. For example, an associated fixed, nonrotating shroud or other form of housing, cowling, case, cover, wall, sheet, lid, beam, frame, or other structure may be configured to continuously resist the free passage of at least a portion of the rotating margin of the flexible, deformable, elastic bluntwheel. Thus the impingement of the nonrotating shroud onto the spinning bluntwheel causes the flexible, elastic bluntwheel to dynamically and continuously assume a non-disk-like shape, the form of which persists in fixed position to the nonrotating shroud even while the flexible, deformable, elastic bluntwheel is itself spinning. The continuous, spatially fixed deformation of the edge of a spinning flexible, elastic bluntwheel is not unlike a standing wave, where the speed of a passing medium exactly equals the wave propagation speed in that medium. In this fashion, any desired stable deformation of a flexible, deformable, elastic bluntwheel can be achieved and maintained.

In one embodiment of a differential dissecting instrument employing a nonrotating shroud to create a stable deformation in a substantially transverse, driveshaft-mounted, spinning flexible, deformable, elastic bluntwheel, the nonrotating shroud is configured to deform the flexible bluntwheel into a substantially folded shape, where the opposite edges of a flexible bluntwheel continuously come together in a substantial apposed fashion. This configuration resembles a soft taco, where the flexible circular sheet is gently folded. This stable, continuous deformation by the nonrotating shroud of a spinning elastic bluntwheel ensures that the two opposed, and apposed, edges of the bluntwheel sporting differentially dissecting tissue engaging projections that are exposed distally by the nonrotating shroud are passing in opposite directions in a manner not unlike that of the exposed portions of two apposed bluntwheels counter-rotating about a common axis.

In either case, whether employing two counter-rotating bluntwheels or employing one folded, spinning bluntwheel, the complex tissue to be dissected encounters the distal-most edges of twin counter-rotating bluntwheels, each edge featuring tissue-engaging projections, which differentially dissect the complex tissue.

In another embodiment, the achievement of distally exposing twin edges of tissue engaging projections is created by employing twin bent bluntwheels, that is, bluntwheels which deviate slightly from a planar form, and whose centers of rotation are roughly similar, but whose axes of rotation are not parallel. These apposed, bent bluntwheels also sport crown gears on their apposed faces and these can be engaged by a bevel pinion gear atop a drive shaft passing from a proximal location (such as the handle of the differential dissection instrument, or the surgical robot) distally to a location between the apposed bent bluntwheels. When the drive shaft rotates, one bent bluntwheel is rotated clockwise about its axis of rotation, while simultaneously the second, apposed bent bluntwheel is rotated counterclockwise, so that twin sets of blunt, differentially dissecting, tissue-engaging projections pass closely in opposing directions, thus differentially dissecting a complex tissue when impinged upon it.

BRIEF DESCRIPTION OF THE FIGURES

FIG. 6 shows a view of the bluntwheels from both FIG. 4 and FIG. 5, here shown together and apposed, rotating in counter-rotating fashion about a substantially common axis.

FIG. 7 depicts a cross-sectional side view of the two bluntwheels shown in FIG. 6, including the direction of motion of the mass of each bluntwheel closest to the viewer as the pair of bluntwheels counter-rotate about a substantially common axis.

FIG. 8 shows an external side view of the two bluntwheels shown in FIG. 6 and FIG. 7, including the direction of motion of the mass of each bluntwheel closest to the viewer as the pair of bluntwheels counter-rotate about a substantially common axis.

FIG. 11 shows an axial view of a rotatable, flexible, elastic bluntwheel mounted on a drive shaft.

FIG. 12 shows a cross-sectional, side view of the rotatable, flexible, elastic bluntwheel mounted on a drive shaft;

FIG. 13 shows an external, side view of the rotatable, flexible bluntwheel mounted to the drive shaft.

FIG. 23 depicts a cross-sectional side view of a driveshaft-mounted, rotatable, hollow, flexible, elastic bluntcone, where the bluntcone is forced to fold by a nonrotatable rigid shroud of non-circular cross-section.

FIG. 24 shows an external front view of the driveshaft-mounted, rotatable, hollow, flexible, elastic bluntcone in FIG. 23, where the bluntcone is forced to fold by a nonrotatable rigid shroud of non-circular cross-section.

FIG. 25 illustrates an internal front view of the driveshaft-mounted, rotatable, hollow, flexible, elastic bluntcone in FIG. 24, where the bluntcone is forced to fold by a nonrotatable rigid shroud of non-circular cross-section.

DETAILED DESCRIPTION

Figure 3:
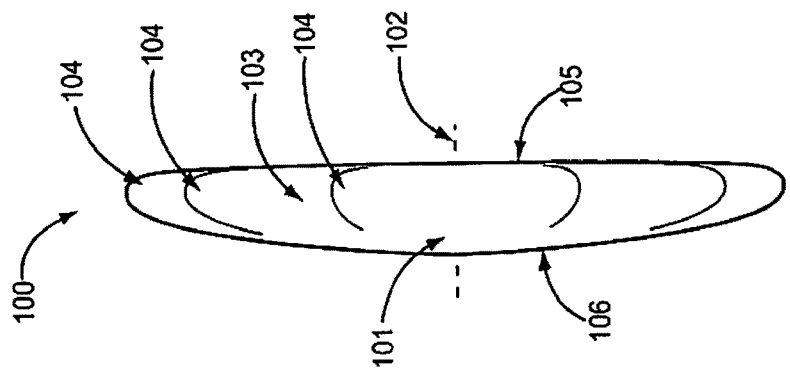
FIG. 3 shows an exterior side view of the bluntwheel, illustrating its curved and flat faces.
Figure 2:
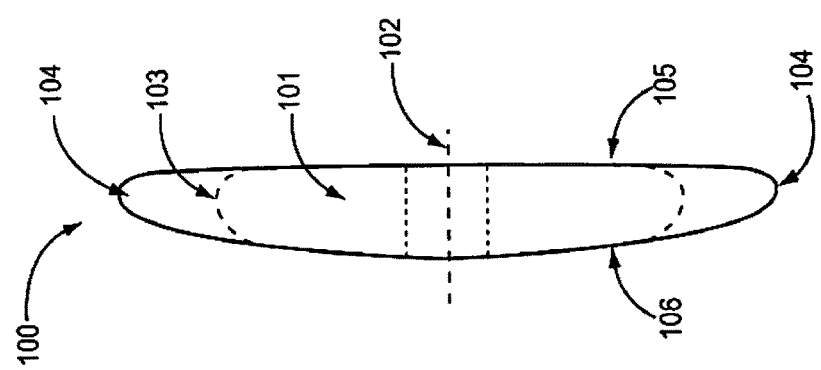
FIG. 2 shows a cross-sectional side view of the bluntwheel, illustrating its curved and flat faces.
Figure 1:
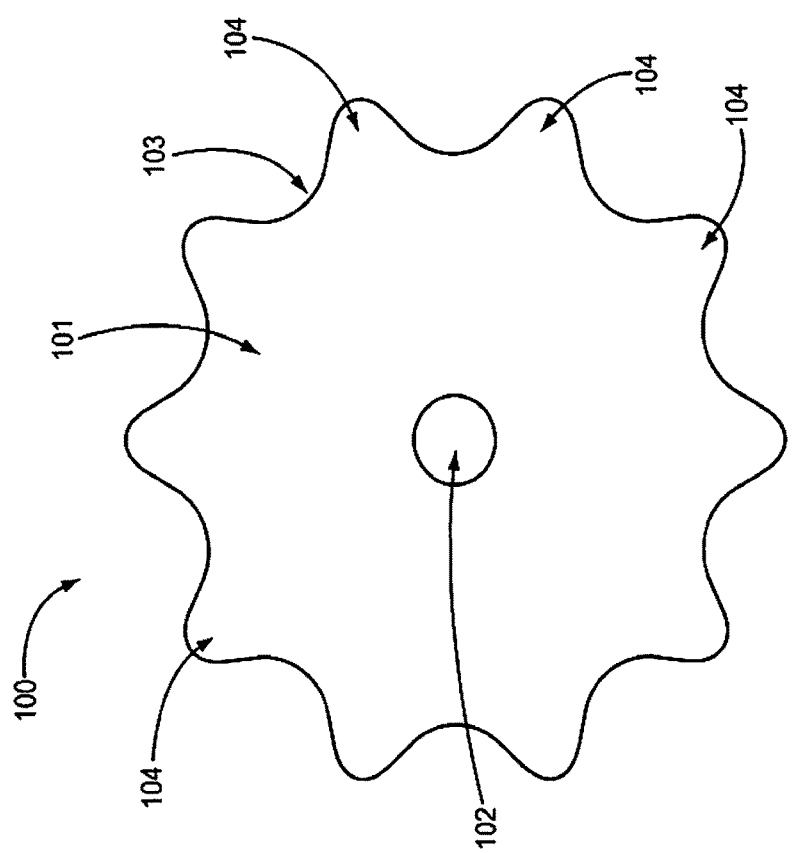
FIG. 1 shows the form of an exemplary bluntwheel for a differential dissecting instrument for dissecting complex tissue, the bluntwheel possessing tissue-engaging projections about its edge, the bluntwheel here viewed along the bluntwheel's rotational axis.

FIGS. 1 through 3 show views of an exemplary bluntwheel 100 for a differential dissecting instrument for dissecting complex tissue. FIG. 1 shows a front view of the form of a bluntwheel 100 when viewed along a rotational axis 102. The bluntwheel 100 has a body 101 and an edge 103 comprising or substantially formed by a plurality of tissue-engaging projections 104 extending radially outward from the center 102. The bluntwheel 100 is rotatable about the rotational axis 102 in one embodiment.

FIG. 2 shows a cross-section of the bluntwheel 100, illustrating its roughly flattened, planar form. In FIG. 2, the body 101 of the bluntwheel 100 possesses a curved face 106 and a flat face 105, an axis of rotation 102 oriented parallel to the plane of the page, and tissue engaging projections 104 extending radially from an edge 103.

FIG. 3 shows an exterior side view of the bluntwheel 100, with its body 101, a curved face 106 and a flat face 105, an axis of rotation 102 parallel to the plane of the page, and a plurality of tissue engaging projections 104. Some embodiments of the bluntwheel 100 can be formed out of a high-modulus material, for example possessing a Young's modulus of one gigapascal or more, for example, stainless steel or medical-grade PEEK, whereas other embodiments of the bluntwheel 100 are preferably formed out a low-modulus material, for example possessing a Young's modulus of one megapascal or less, for example polyurethane elastomer. The orientation of the roughly planar bluntwheel 100 with respect to the rest of the differential dissection instrument depends on each embodiment, as we disclose below.

Figure 5:
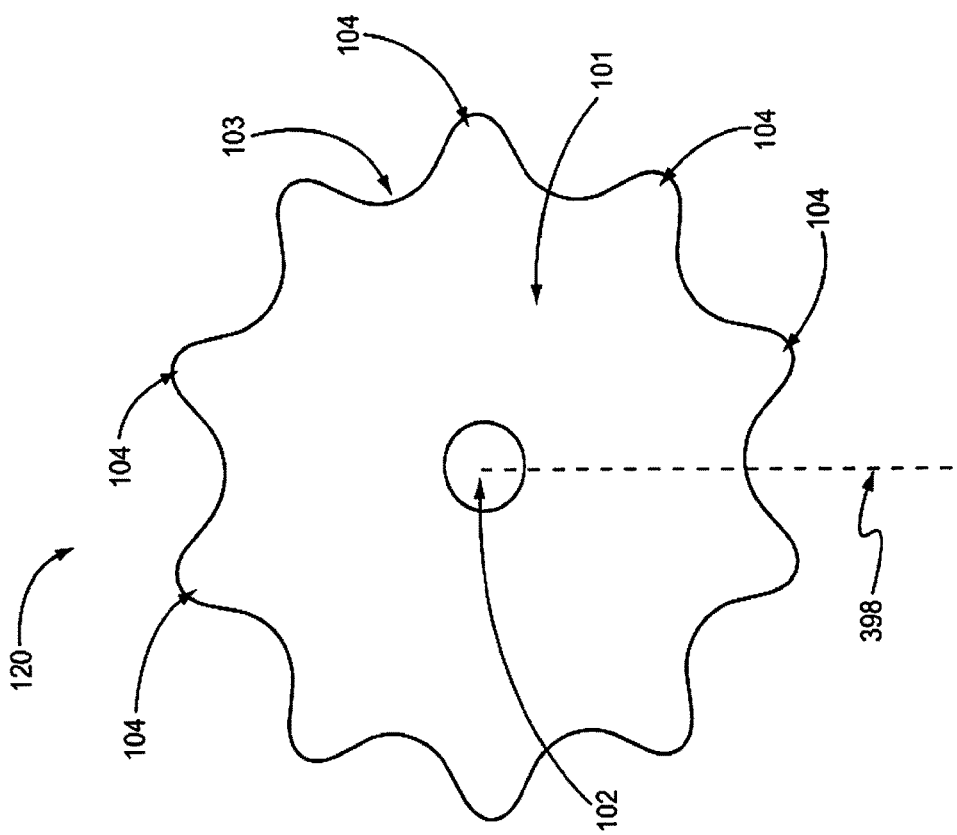
FIGS. 4 and 5 each show the forms of each half of a bluntwheel pair, and each viewed along its rotational axis; these two bluntwheels can each rotate about their centers.
Figure 4:
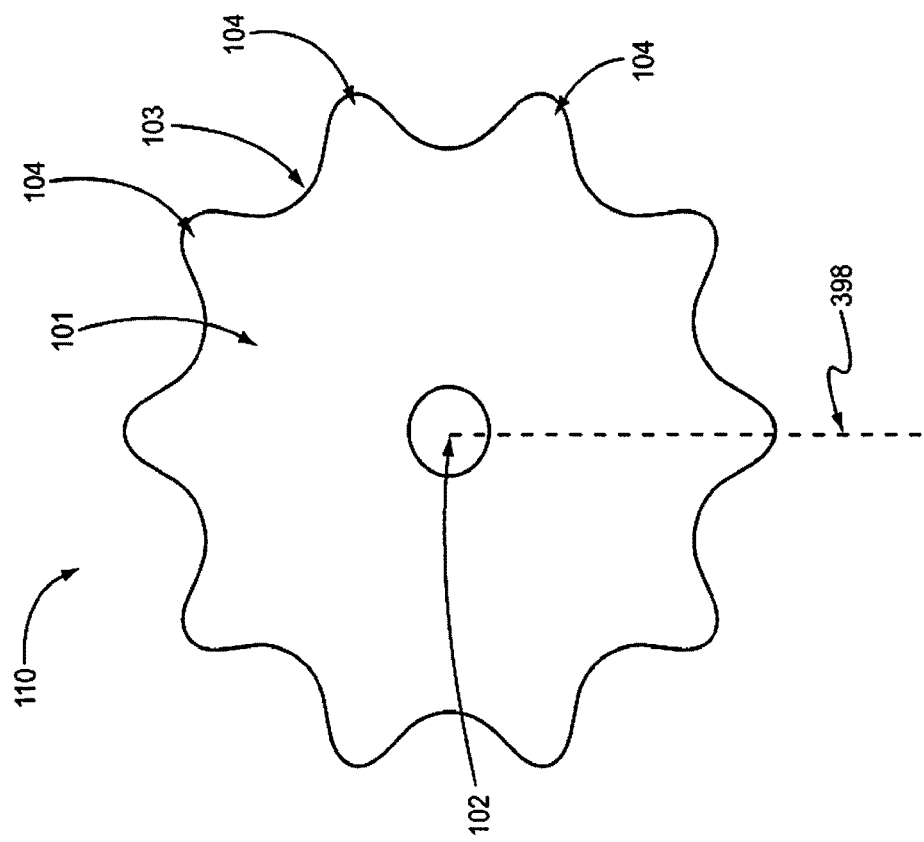

FIGS. 4 and 5 each show the form of a first half of a bluntwheel pair 110 and the form of a second half of a bluntwheel pair 120, respectively, where each is viewed along its rotational axis 102 and is rotatable. Each half 110 and 120 possesses a body 101 and an edge 103 comprising or substantially formed by a plurality of tissue-engaging projections 104 extending radially outward from the center 102. Together these two bluntwheels comprise a pair of apposed bluntwheels 110 and 120 that can each rotate about an axis of rotation 102, where the two rotational axes can be substantially coaxial. The orientation of the axes of rotation 102 with respect to the long axis 398 of the differential dissection instrument depends on the configuration of the embodiment, as disclosed below.

FIG. 6 shows a view of an embodiment 130 of a differential dissecting device, comprising the bluntwheels 110 and 120 from FIG. 4 and FIG. 5, here shown with the axes of rotation 102 pointing out of the plane of the page. In FIG. 6 the bluntwheels 110 and 120 are shown together with their flat sides apposed, rotating in counter-rotating fashion about a substantially common axis 102, where the bluntwheel 110 from FIG. 4 is shown closer to the viewer and rotating clockwise (arrow 150) about the common axis 102, while the bluntwheel 120 from FIG. 5 is shown farther from the viewer and rotating counterclockwise (arrow 151) about the common axis 102. The substantially common axis 102 is, in this embodiment, oriented at 90° to a long axis 398 of the differential dissection instrument, and the plurality of tissue engaging projections 104 are being carried along with their respective bluntwheel, thereby presenting a differential dissecting action to the complex tissue to be dissected. The long axis 398 further possesses a proximal end 501 directed at the user or surgical machine, which can be motorized, and a distal end 502 directed at the complex tissue to be dissected. This embodiment, when activated, thus presents the two opposed passing sets of tissue engaging projections 104 distally to the complex tissue to be dissected, differentially dissecting the complex tissue, enabling safer and faster blunt dissection during surgical procedures.

FIG. 7 depicts a cross-sectional side view of the embodiment 130 of the two bluntwheels 110 and 120 shown in FIG. 6, with the long axis 398 of the surgical instrument shown oriented vertically, forming a 90° angle with respect to the (in this view, transverse) axis of rotation 102. In FIG. 7, it can be seen that the flat faces 105 of the bluntwheels are apposed, leaving the curved faces 106 facing away from each other. The bluntwheels 110 and 120 are rotatably associated and are configured to rotate about a substantially common axis of rotation 102. FIG. 7 also shows that the clockwise rotation 150 of the bluntwheel 110 is directly opposite the counterclockwise rotation 151 of the bluntwheel 120, thus carrying each bluntwheel's plurality of tissue engaging projections 104 past the other plurality of tissue engaging projections 104, thereby presenting a differential dissecting action to the complex tissue to be dissected. The long axis 398 possesses a proximal end 501 directed at the user and a distal end 502 directed at the complex tissue to be dissected. At the top of FIG. 7, it can be seen that the two sets of tissue engaging projections 104 pass either out of (for bluntwheel 110) or into (for bluntwheel 120) the plane of the page, thus presenting two opposed passing sets of tissue engaging projections 104 distally to the complex tissue to be dissected, differentially dissecting the complex tissue.

FIG. 8 shows an external side view of the embodiment 130 comprising the two rotatably associated bluntwheels 110 and 120 shown in and FIG. 7, again showing that their opposing flat faces 105 are directly apposed, with their curved faces 106 facing away from one another, and depicting the direction of motion of each bluntwheel (150 for bluntwheel 110, and 151 for bluntwheel 120) as the pair of bluntwheels counter-rotate about a substantially common axis 102, which is itself perpendicular to the long axis 398 of a surgical instrument located near the proximal end 501. The surgical instrument may be motorized, such that when operated it presents to the distal end 502 a plurality of tissue engaging projections 104 to the complex tissue to be dissected.

Figure 9:
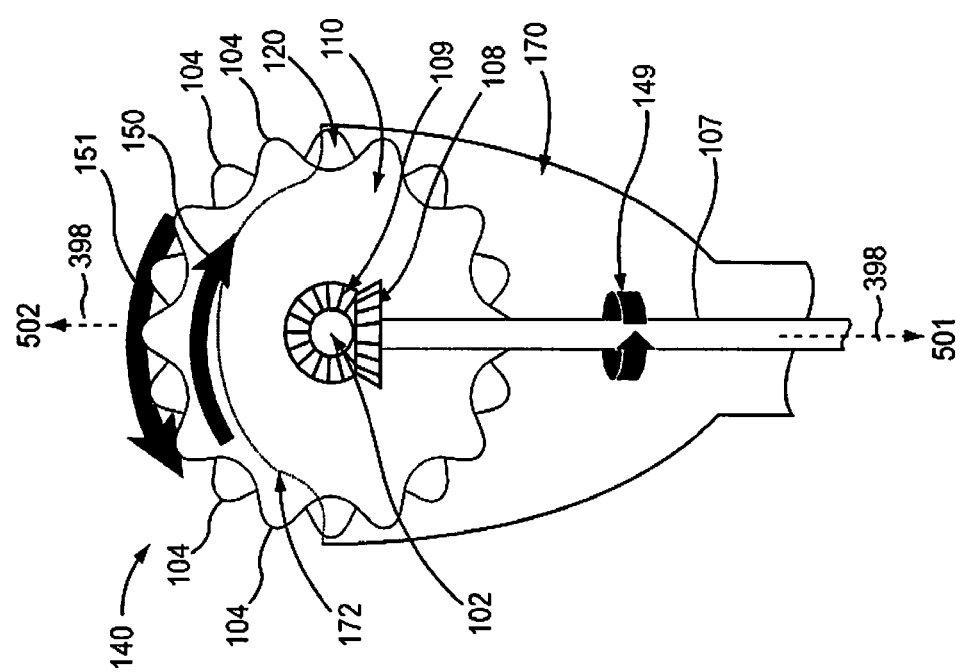
FIG. 9 shows a cross-sectional view of an embodiment of the distal portion of a differential dissection instrument, depicting an assembly of two bluntwheels in apposition and configured to counter-rotate about a common axis.

FIG. 9 shows a cross-sectional view of an embodiment of the distal portion of a differential dissection instrument, depicting an assembly 140 of two bluntwheels 110 and 120 with their flat faces 105 in apposition and configured to counter-rotate (black arrows 150 and 151) about a substantially coaxial, common axis of rotation 102. The axis of rotation 102 is oriented substantially transversely to a long axis 398 of a differential dissection instrument. The long axis 398 further possesses a proximal end 501 directed at a user or surgical machine, which may be motorized, and a distal end 502 directed at a complex tissue to be dissected. The two bluntwheels 110 and 120 each possess a plurality of tissue engaging projections 104. Each bluntwheel further comprises an affixed crown gear 109 that is located on each bluntwheel's flat face 105 and is coaxial to each bluntwheel's axis of rotation 102. The assembly 140 further comprises a drive shaft 107 substantially aligned with the long axis 398 and rotatable about it. The driveshaft 107 further may be rotatably associated with the surgical machine near the proximal end 501 of the long axis 398, and further may possess a pinion bevel gear 108 affixed to its distal-most end and meshing with the two crown gears 109 on the flat faces 105 of the bluntwheels 110 and 120. The pinion bevel gear 108 is configured so that when the drive shaft 107 rotates (black arrow 149), it drives the affixed pinion bevel gear 108, and so drives the counter-rotation (black arrows 150 and 151) of the bluntwheels 110 and 120, thus presenting to the complex tissue to be dissected two opposed passing sets of tissue engaging projections 104 distally, thus differentially dissecting the complex tissue. The assembly further comprises a shroud 170 which covers and protects the differential dissection instrument 130 from the patient's tissues and vice versa, and can provide support for locating the bluntwheels 110 and 120 and drive shaft 107.

Figure 10:
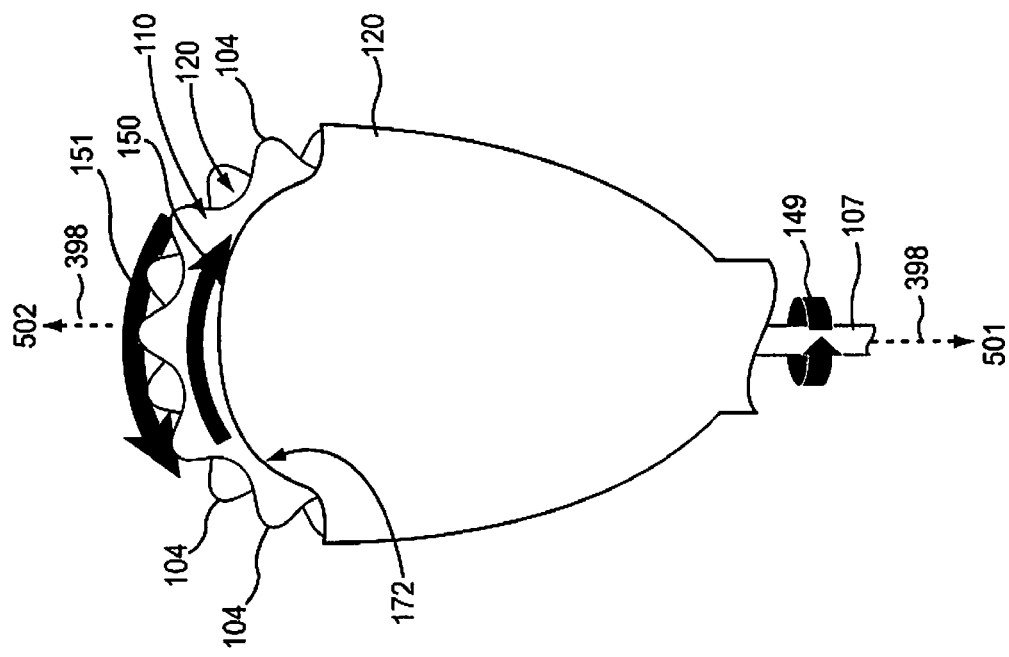
FIG. 10 shows an external view of the differential dissector embodiment depicted in FIG. 9.

FIG. 10 is an external view of the embodiment depicted in FIG. 9, also showing the rotary input 149 of the drive shaft 107 and the resulting counter-rotational outputs (150 and 151) of the bluntwheels 110 and 120. It is clear that the shroud 170 can cover most of the assembly 140 while leaving just the distal portion of the counter-rotating bluntwheels to effect differential dissection of the complex tissue to be dissected.

FIG. 11 through FIG. 13 show the form of a driveshaft-mounted, flexible, elastic bluntwheel 200, possessing a roughly disk-like, planar body 101C shown oriented perpendicular to a long axis 398 of a surgical instrument. The bluntwheel 200 also comprises a curved face 106 here facing proximally, a flat face 105 facing distally, an edge 103 comprised of a plurality of radially extending tissue engaging projections 104, a drive shaft 107, and a means 102A to affix the body 101C to the drive shaft 107. The bluntwheel 200 shares an axis of rotation 102 with the drive shaft 107.

Note that as long as the elastic, roughly disk-like, planar body 101C is unstressed, it will remain substantially planar, at rest, unloaded, until acted upon. Long axis 398 comprises a proximal end directed at a user or surgical machine, which may be motorized, and a distal end directed at a complex tissue to be dissected.

FIG. 11 shows the axial view of the driveshaft-mounted, flexible, elastic bluntwheel 200.

FIG. 12 shows a cross-sectional, side view of the driveshaft-mounted, flexible, elastic bluntwheel 200, showing that the axis of rotation 102 is coincident with the long axis 398, so that this embodiment rotates transversely about the long axis 398. FIG. 13 shows an external, side view of the driveshaft-mounted, flexible, elastic bluntwheel 200. The embodiment 200 further comprises a long axis 398, which itself has a proximal end 501 directed proximally toward a user or surgical machine, which may be motorized, and a distal end 502 directed at the complex tissue to be dissected. The bluntwheel 200 has a body 101C, here formed of flexible, elastic material, which may be of a low Young's modulus, for example roughly one megapascal, and can be a polyurethane elastomer or any other medically appropriate material. It is important to note that the flexible, elastic bluntwheel 200 is non-rigid and so can be deflected out-of-plane, that is, this bluntwheel 200 can be deformed, folded, stressed, strained, or otherwise deflected by anything that impinges strongly enough upon it. This folding can be due to a static load, or it can be due to a dynamic load, or it can be of arbitrary form, as desired by the designer. Thus the folding can be an intentional, configurable outcome of the various embodiments described below. As before, the edges 103 of such bluntwheels 200 possess a series of tissue engaging projections 104 configured for the differential dissection of a complex tissue brought into contact with it by the surgeon.

Figure 14:
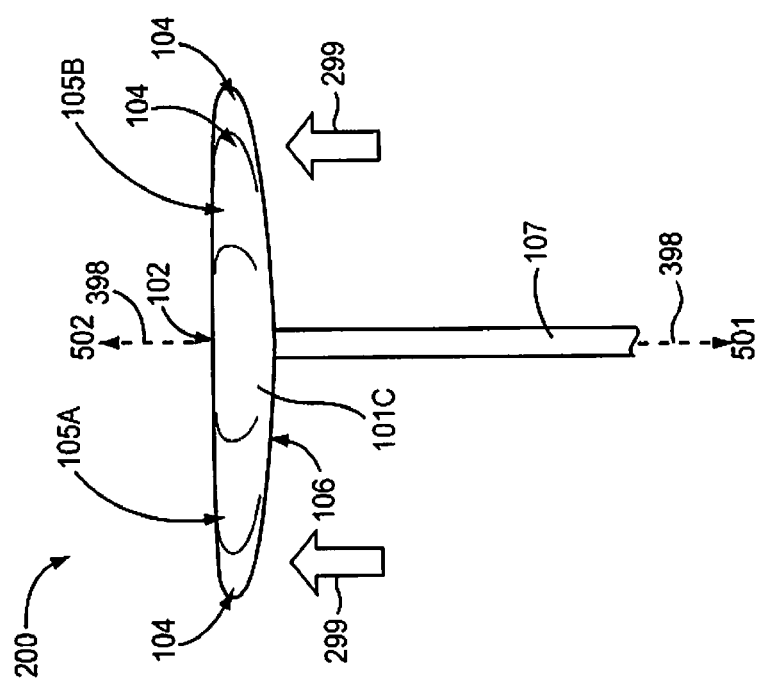
FIG. 14 shows an external side view of the driveshaft-mounted, rotatable, flexible, elastic bluntwheel before it is deformed.

FIG. 14 is identical to FIG. 13, save for the labeled presence of first, distally directed, impinging forces 299, which can act to deflect the elastic, flexible body 101C of bluntwheel 200, and second, diametrically opposite portions 105A and 105B of the distally directed, flat face 105. The impinging forces 299 are shown in this view as incipient, and not yet deflecting the body 101C of bluntwheel 200.

Figure 15:
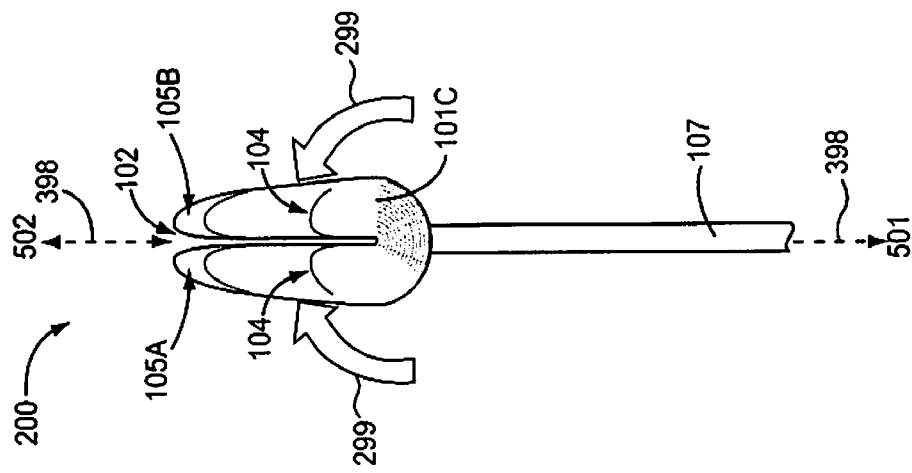
FIG. 15 shows an external side view of the same rotatable, flexible bluntwheel as it is deformed.

FIG. 15 illustrates that the impinging forces 299 have now acted to fold the body 101C of the driveshaft-mounted, flexible, elastic bluntwheel 200 distally until the diametrically opposite portions 105A and 105B of the distally directed, flat face 105 have now contacted one another, and are thus substantially apposed. Since the now folded body 101C is elastic, the curved face 106 is now stretched, while flat face 105 is now compressed, and the body 101C of the bluntwheel 200 is thus elastically loaded, like a spring, storing the energy from the impinging forces 299, and so the body 101C would immediately recoil back to a flat shape if released.

Together, FIG. 14 and FIG. 15 depict two stages in the deformation of the body 101C of the driveshaft-mounted, flexible, elastic bluntwheel 200. Thus, FIG. 14 shows an external side view of the driveshaft-mounted flexible, elastic, disk-like, roughly planar bluntwheel 200 before it is deformed, and FIG. 15 shows an external side view of the same flexible, elastic bluntwheel 200 while it is deformed by the impinging forces 299, here folding the flexible, elastic bluntwheel 200 distally like a taco until the diametrically opposed flat faces 105A and 105B of opposite edges of the flexible, elastic bluntwheel substantially meet, thus placing two sets of a plurality of tissue engaging projections 104 in apposition, distally, directed toward 502 and so the complex tissue to be dissected.

Figure 16:
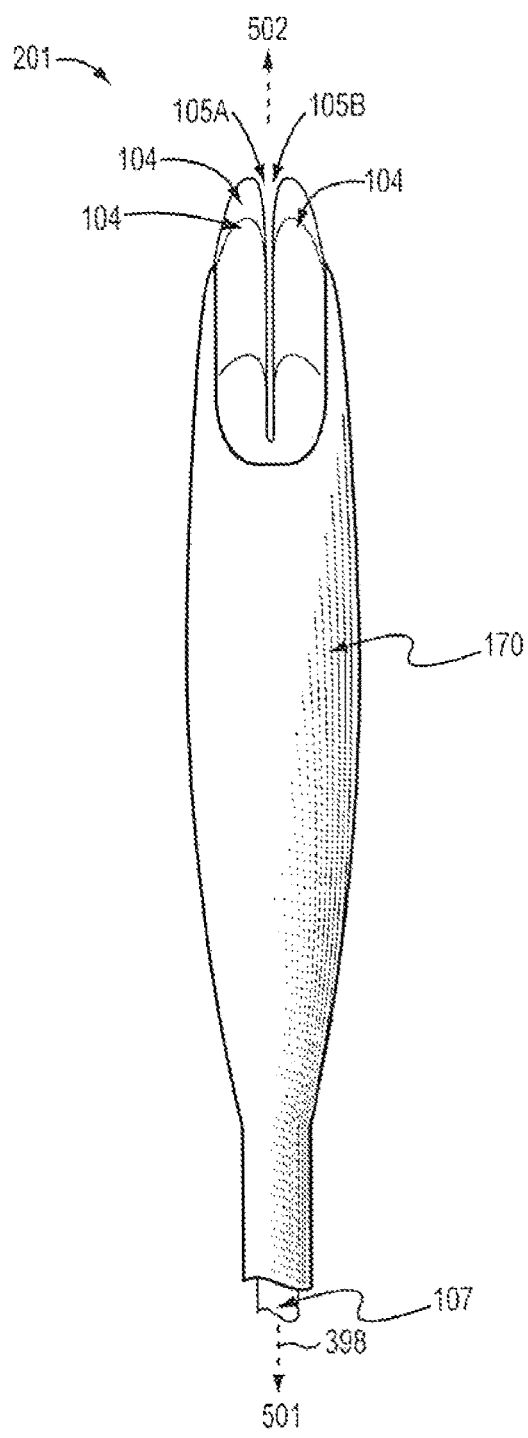
FIG. 16 illustrates in external side view the driveshaft-mounted, rotatable, flexible, elastic bluntwheel as it is forced by a shroud to fold while spinning.

FIG. 16 illustrates in external side view another embodiment of a bluntwheel assembly 201. FIG. 16 is identical to FIG. 15, save for the inclusion of a nonrotating, non-circular shroud 170, which, given its placement as seen in this view, is the source of the impinging forces 299 in FIG. 15. Thus the shroud 170 loads the elastic body 101C, and so brings into distal apposition the diametrically opposed faces 105A and 105B of the flat face 105 of the driveshaft-mounted, flexible, elastic bluntwheel 201. Thus the bluntwheel 201 is folded as shown in FIG. 15 and is protected, so is forced to deform by folding, and supported in folded form by an encompassing rigid shroud 170. In cutaway fashion, it is shown where the drive shaft (shown vertical in this view) resides within the non-circular shroud 170, which in this view is narrow.

Figure 17:
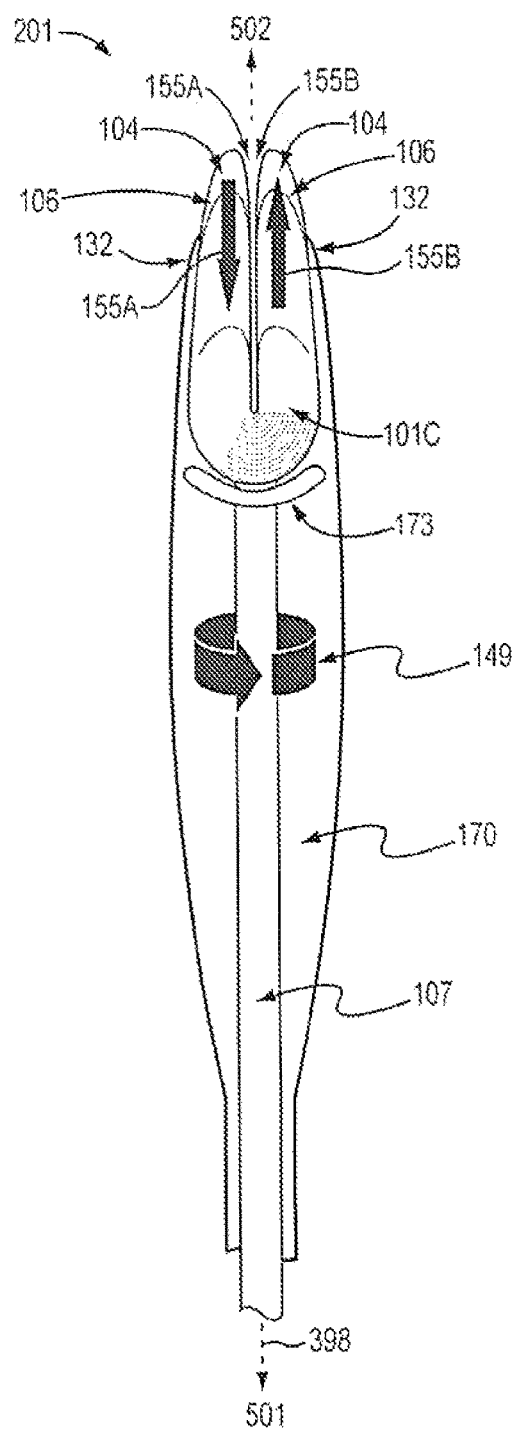
FIG. 17 depicts in cross-sectional, side view the internal structures of the driveshaft-mounted, rotatable, flexible, elastic bluntwheel as illustrated in FIG. 16, where the bluntwheel is forced to fold while spinning inside a shroud.

FIG. 17 depicts in cross-sectional, side view the internal structures of the driveshaft-mounted, flexible, elastic bluntwheel 201 as illustrated in FIG. 16. In FIG. 17, the flexible, elastic bluntwheel 201 is shown similarly folded, and here is further shown protected, forced to deform by folding, and supported in folded form by a rigid shroud 170 of non-circular cross-section (narrow in this view). In FIG. 17, there is also depicted an internal support 173 in the form of a curved plate located proximal to the body 101C of the flexible, elastic bluntwheel. The internal support 173 assists the shroud 170 in maintaining the distally folded form of the body 101C of the flexible, elastic bluntwheel and through which the driveshaft 107 passes via orifice 174. The drive shaft 107 is also shown vertical and exposed, and showing its rotation 149 about the long axis 398 and where the resulting motion (black arrows 155A and 155B) of the associated driveshaft-mounted flexible, elastic bluntwheel 201 is clearly seen. The resulting apposed, opposed, counter-rotating motions 155A and 155B of the projections 104 on the two edges of the flexible, elastic bluntwheel that have been brought into apposition by the presence of the non-circular shroud 170, display exposed behavior, not unlike the distal-most effects of the two counter-rotating bluntwheels 110 and 120 depicted in FIG. 9 and FIG. 10.

Figure 18:
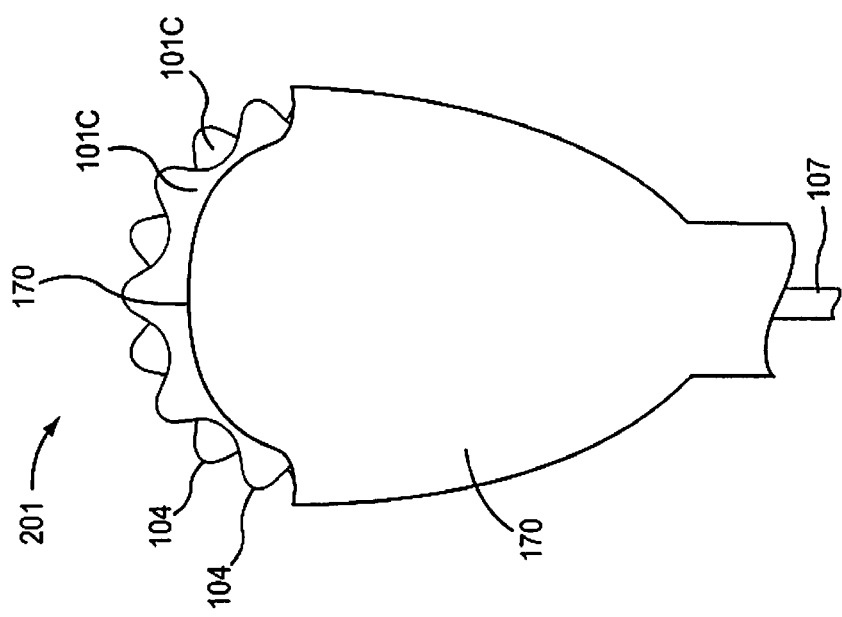
FIG. 18 depicts in external front view the driveshaft-mounted, rotatable, flexible, elastic bluntwheel as it is forced by a shroud to fold while spinning as illustrated in FIG. 16.

FIG. 18 depicts the embodiment shown in FIG. 16, in external view and with the driveshaft 107 oriented vertically within the plane of the page. In FIG. 18, the driveshaft 107 is shown parallel and perpendicular to FIG. 16, so that the non-circular shroud 170 appears wide. In FIG. 18, the body 101C of the flexible, elastic bluntwheel is shown protected, forced to deform by folding, and supported in folded form by the non-circular shroud 170 and also by the shroud edge 172.

Figure 19:
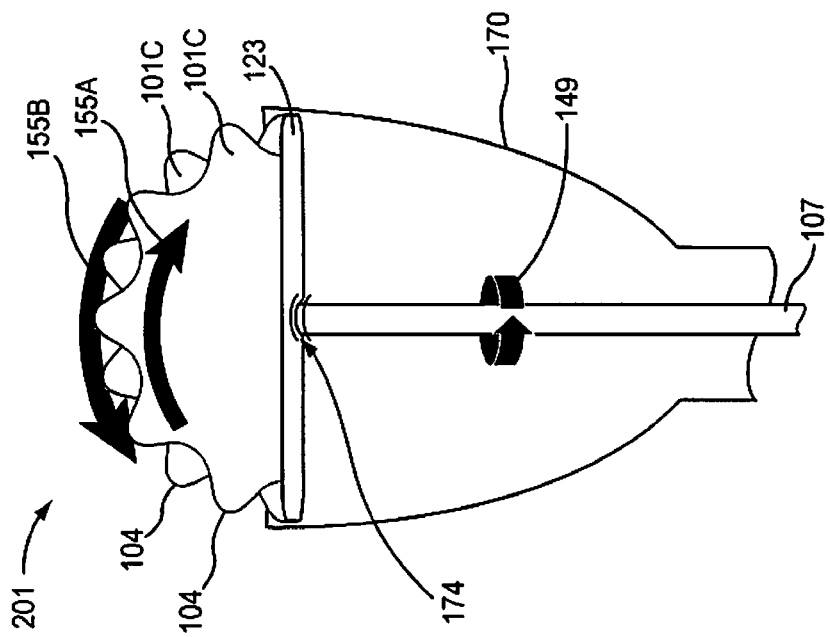
FIG. 19 shows in cross-sectional view the internal structures of the driveshaft-mounted, rotatable, flexible, elastic bluntwheel in FIG. 18, where the bluntwheel is forced to fold while spinning inside a shroud.

FIG. 19 shows 201, the driveshaft-mounted, flexible, elastic bluntwheel as illustrated in FIG. 18, in cross-sectional, internal view. FIG. 19 shows the body 101C of the flexible, elastic bluntwheel 201 shown protected, forced to deform distally by folding, and supported in distally folded form by the rigid shroud 170 of non-circular cross-section. FIG. 19 also depicts an internal support in the form of a curved plane 173 that is proximally assisting the shroud 170 in maintaining the distally folded form of the flexible, elastic bluntwheel 101C and a hole 174 through which the driveshaft 107 passes. In FIG. 19 the driveshaft 107 is also shown vertical and exposed, and showing its rotation 149 about its long axis 398 and the resulting motion 155A and 155B of the associated driveshaft-mounted flexible, elastic bluntwheel is clearly seen, including the resulting distally apposed, counter-rotating motions 155A and 155B of the projections 104 on the two edges 103 of the flexible, elastic bluntwheel that have been brought into apposition by the presence of the non-circular shroud 170, with exposed behavior not unlike the distal-most effects of the two counter-rotating bluntwheels 110 and 120 depicted in FIG. 9 and FIG. 10.

Referring now to FIG. 20 through FIG. 25, these depict embodiments 300 and 301 of driveshaft-mounted, hollow, rotatable, flexible, deformable, elastic cones bearing tissue-engaging projections 104 along their distal-most edges, and caused to deform into a twin set of distally, externally counter-rotating differentially dissecting edges by a nonrotating shroud 170. Hereinafter, a cone similar to the cones referred to in the above sentence and shown in FIG. 20 through FIG. 25 is referred to as a "bluntcone."

Figure 20:
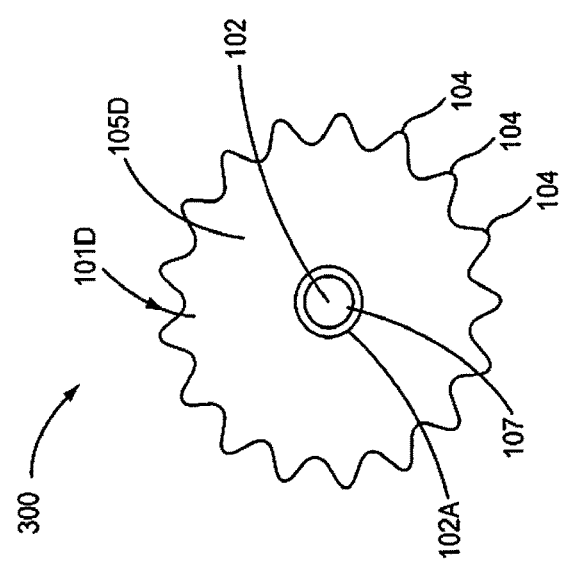
FIG. 20 shows the form of a driveshaft-mounted, rotatable, hollow, flexible, elastic bluntcone when viewed proximally along its rotational axis.

First, FIG. 20 shows the form 300 of the driveshaft-mounted, hollow, flexible, elastic bluntcone when viewed proximally, along its rotational axis 102, toward the user, handle, or surgical machine. The device 300 here has a long axis 398, which itself has a user direction 501 directed proximally, and a tissue direction 502, directed distally toward a complex tissue to be dissected. The bluntcone 300 has a body 101D, possessing a center 102 where it joins affixed at 102A proximally with a drive shaft 107, and an edge 103, located distal to where the body 101D of the bluntcone 300 joins the drive shaft 300. The edge of the bluntcone 300 possesses a series of tissue engaging projections 104 configured for the differential dissection of a complex tissue brought into contact with it by the surgeon. The bluntcone 300 also has an interior surface 105D directed distally.

Figure 22:
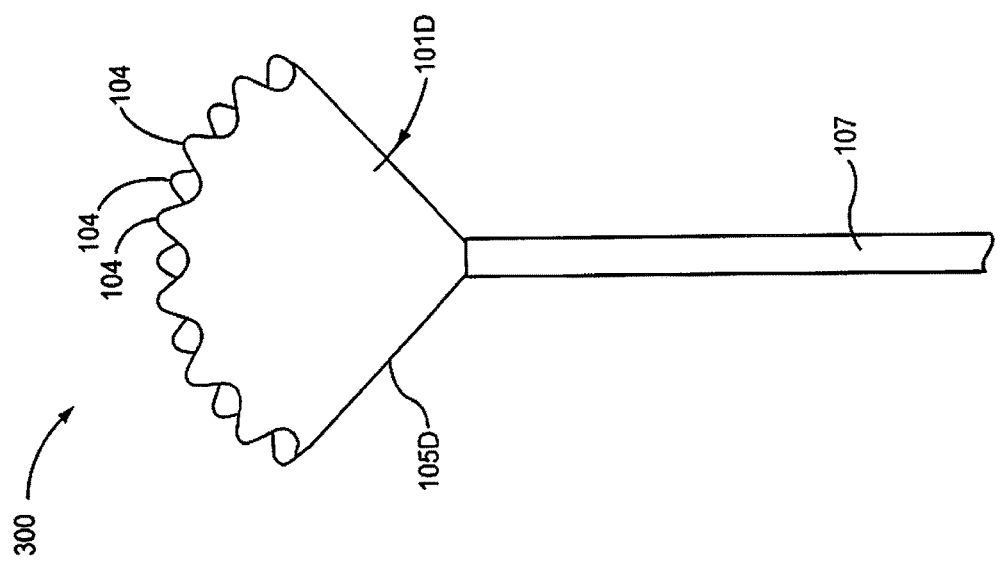
FIG. 22 shows an external view of the rotatable, hollow, flexible bluntcone after it is deformed by folding the flexible, elastic bluntcone until the opposite edges of the flexible, elastic bluntcone substantially meet in apposition.
Figure 21:
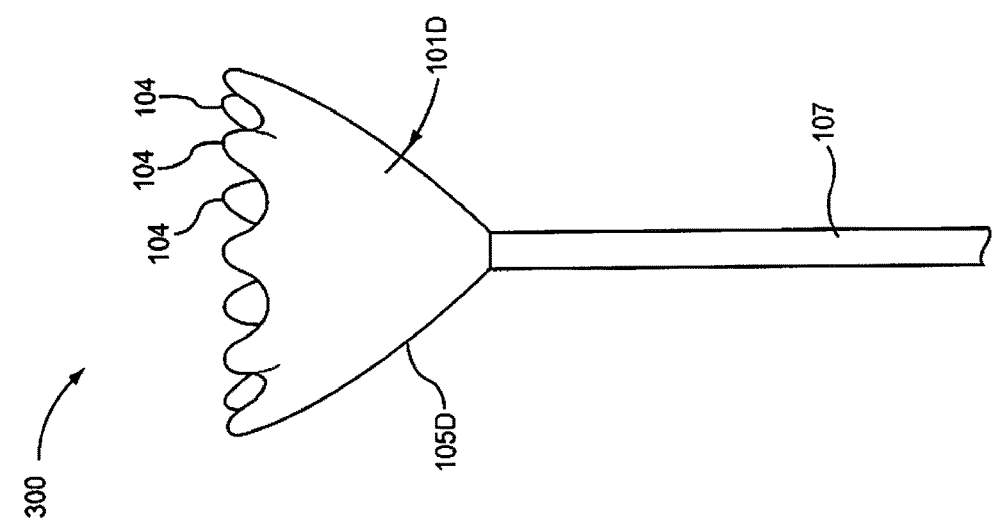
FIG. 21 depicts an external side view of the driveshaft-mounted, rotatable, flexible, elastic bluntcone before the bluntcone is deformed.

FIG. 21 and FIG. 22 depict two stages in the deformation of a hollow, flexible, elastic bluntcone 300 mounted on a drive shaft 107 (oriented vertically in these two FIGS.) and sharing an axis of rotation 102 with the drive shaft. In the first stage, FIG. 21 shows an external side view of the driveshaft-mounted flexible, elastic bluntcone 300 before it is deformed. In the second stage, FIG. 22 shows an external view of the same flexible bluntcone 300 after it is deformed, here, by folding the body 101D of the flexible, elastic bluntcone 300 until the opposite interior faces 105D of opposite edges of the flexible, elastic bluntcone 300 substantially meet in apposition. In both FIG. 21 and FIG. 22, the drive shaft 107 is oriented vertically and parallel to the plane of the page.

FIG. 23 depicts a cross-sectional side view of a driveshaft-mounted, hollow, flexible, elastic bluntcone 301, where the drive shaft 107 is oriented vertically in this image. The bluntcone 300 shares an axis of rotation 102 with the drive shaft. The body 101D of the bluntcone 301 is protected, forced to deform by folding, and supported in folded form by a rigid shroud 170 of non-circular cross-section. Interior face 105D has collapsed into apposition, folding flat, causing tissue engaging projections 104 to form two rows distally.

FIG. 24 shows an external view of the hollow, flexible, elastic bluntcone 301 in a shroud 170 of FIG. 23, with the drive shaft 107 still oriented vertically, but perpendicular to that view, with an orientation similar to FIG. 22. FIG. 24 shows that the body 101D of the bluntcone 301 is forced to deform by folding, and supported in folded form by a rigid shroud 170 of non-circular cross-section.

FIG. 25 illustrates an external view of the hollow, flexible, elastic bluntcone 301 in a shroud 170 of FIG. 24, with the drive shaft 107 still oriented vertically and distally directed distally 502 at a complex tissue to be dissected. In FIG. 25, the vertical driveshaft 107 is shown exposed. FIG. 25 shows the rotation 149 of the driveshaft 107 about its long axis 398, with the resulting induced motion 155A and 155B of the associated driveshaft-mounted flexible, elastic bluntcone 301. Also seen in FIG. 25 is the resulting distally apposed, counter-rotating motions 155A and 155B of the projections 104 on the two edges of the flexible, elastic bluntcone 301 that have been brought into apposition by the presence of the non-circular rigid shroud 170. The exposed behavior of this embodiment is not unlike the distal-most behavior of the two counter-rotating bluntwheels depicted in FIGS. 9, 10, and 19.

Figure 26:
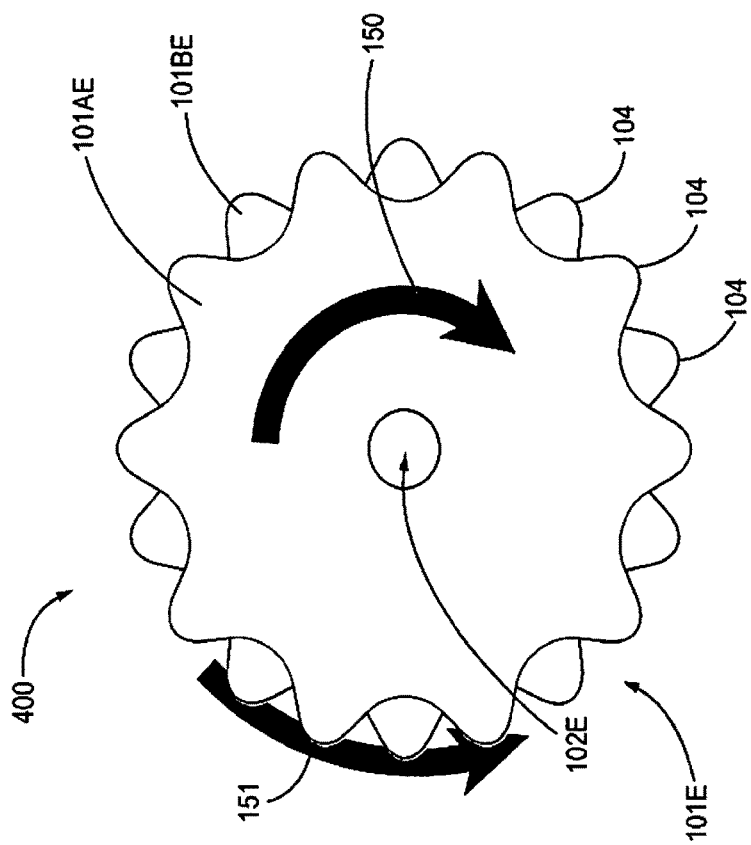
FIG. 26 shows a front view of two bent bluntwheels counter-rotating with respect to one another, with their axes of rotation near each other but not parallel to each other.

FIG. 26 shows embodiment 400, depicting two bent bluntwheels 101AE and 101BE counter-rotating (black arrows 150 and 151) with respect to one another; while their axes of rotation 102E are near each other, the axes of rotation 102E of bent bluntwheels 101AE and 101BE may not be parallel, and neither of the bent bluntwheels 101AE and 101BE is a flat disk.

Figure 27:
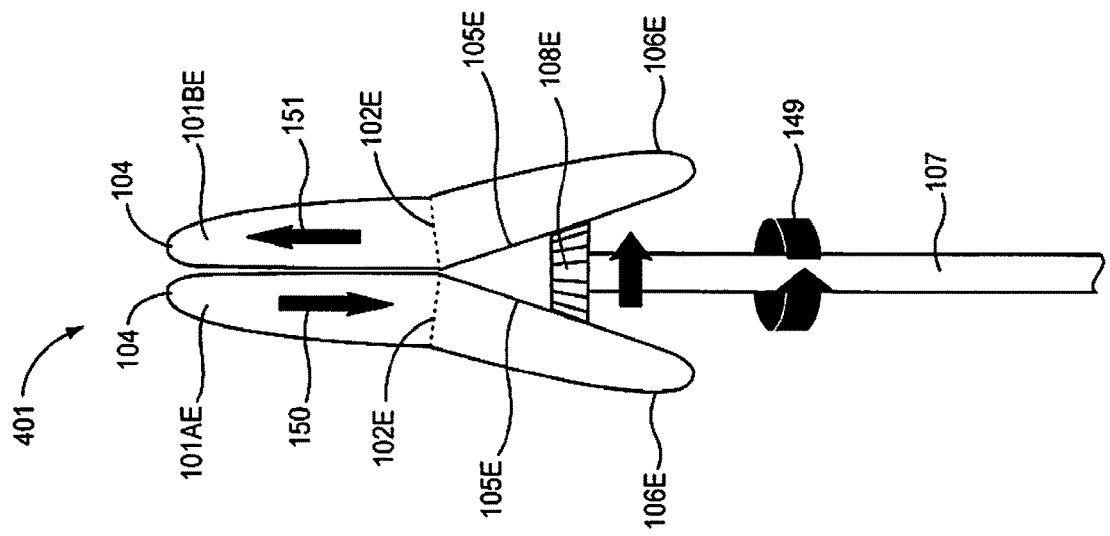
FIG. 27 shows a cross-sectional side view of one embodiment of a bent bluntwheel assembly comprising the pair of bent bluntwheels from FIG. 26 connected by their apposed faces to a driveshaft possessing a bevel pinion gear.

FIG. 27 shows an exposed cross-sectional side view of one embodiment of a bent bluntwheel assembly 401 comprising the pair of bent bluntwheels 101AE and 101BE from FIG. 26, clearly showing their bent form. It can be seen in FIG. 27 that neither of the bent bluntwheels 101AE and 101BE is a flat disk, and that their rotational axes 102E are nonparallel with one another. FIG. 27 also illustrates that this embodiment of a bent bluntwheel assembly 401 includes a vertical drive shaft 107 with a distally located bevel pinion gear 108E, and how this bevel pinion gear 108 can engage a pair of bevel crown gears 105E located on the roughly apposed faces of the two apposed bent bluntwheels 101AE and 101BE; this image also shows the input rotation 149 of the (here, vertical) drive shaft 107 causes the counter-rotating output action (black arrows 150 and 151) of the two apposed bent bluntwheels 101AE and 101BE, thus distally offering a twin set of passing projections 104 to the complex tissue to be dissected, thus performing differential dissection there.

Figure 28:
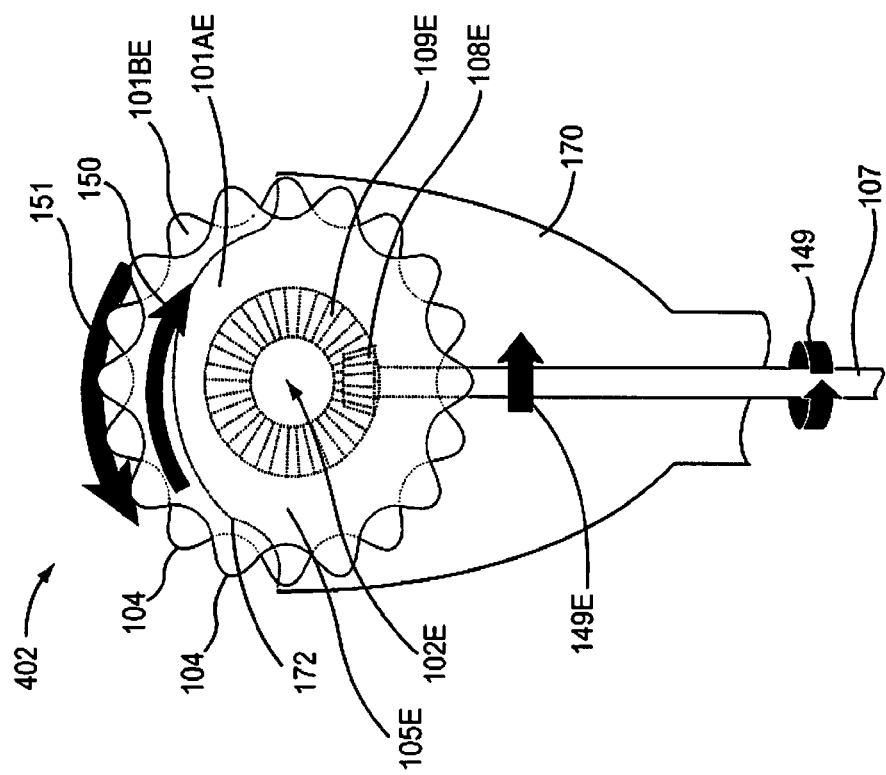
FIG. 28 depicts a cross-sectional front view of the bent bluntwheel assembly depicted in FIG. 27, here also showing a nonrotating shroud, input motion and output motion.

FIG. 28 depicts an embodiment 402 in cross-sectional side view of the bent bluntwheels 101AE and 101BE depicted in FIG. 27, clearly showing the (here, vertical) drive shaft 107 with distally mounted bevel pinion gear 108E engaging crown bevel gears 109E on the apposed faces 105E of two bent bluntwheels 101AE and 101BE. The rotational input 149 of the drive shaft 107 is seen, and it is clear that the drive shaft input 149 results in a counter-rotating action (black arrows 150 and 151) of the two bent bluntwheels 101AE and 101BE. This offers a differential dissection effect at the distal-most portion of the differential dissection instrument, thus differentially dissecting a complex tissue when brought into contact with same.

Figure 29:
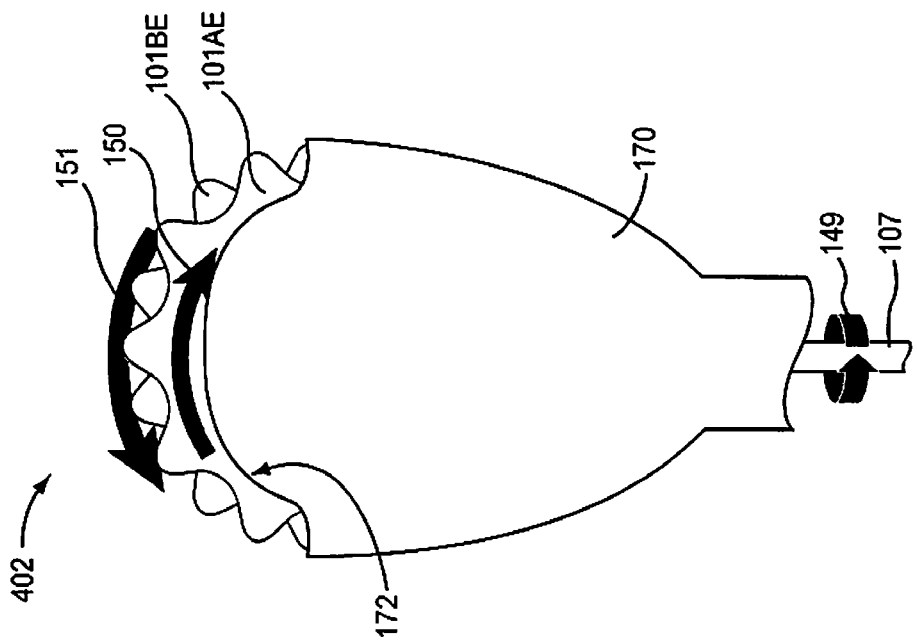
FIG. 29 shows an external view of the bent bluntwheel assembly of FIG. 28.

FIG. 29 shows an external view of FIG. 28, again clearly illustrating how the drive shaft's 107 rotational input 149 results in counter-rotational output 150 and 151 at the exposed projections 104 of the bent bluntwheels 101AE and 101BE, thus differentially dissecting a complex tissue in contact thereof.

Figure 30:
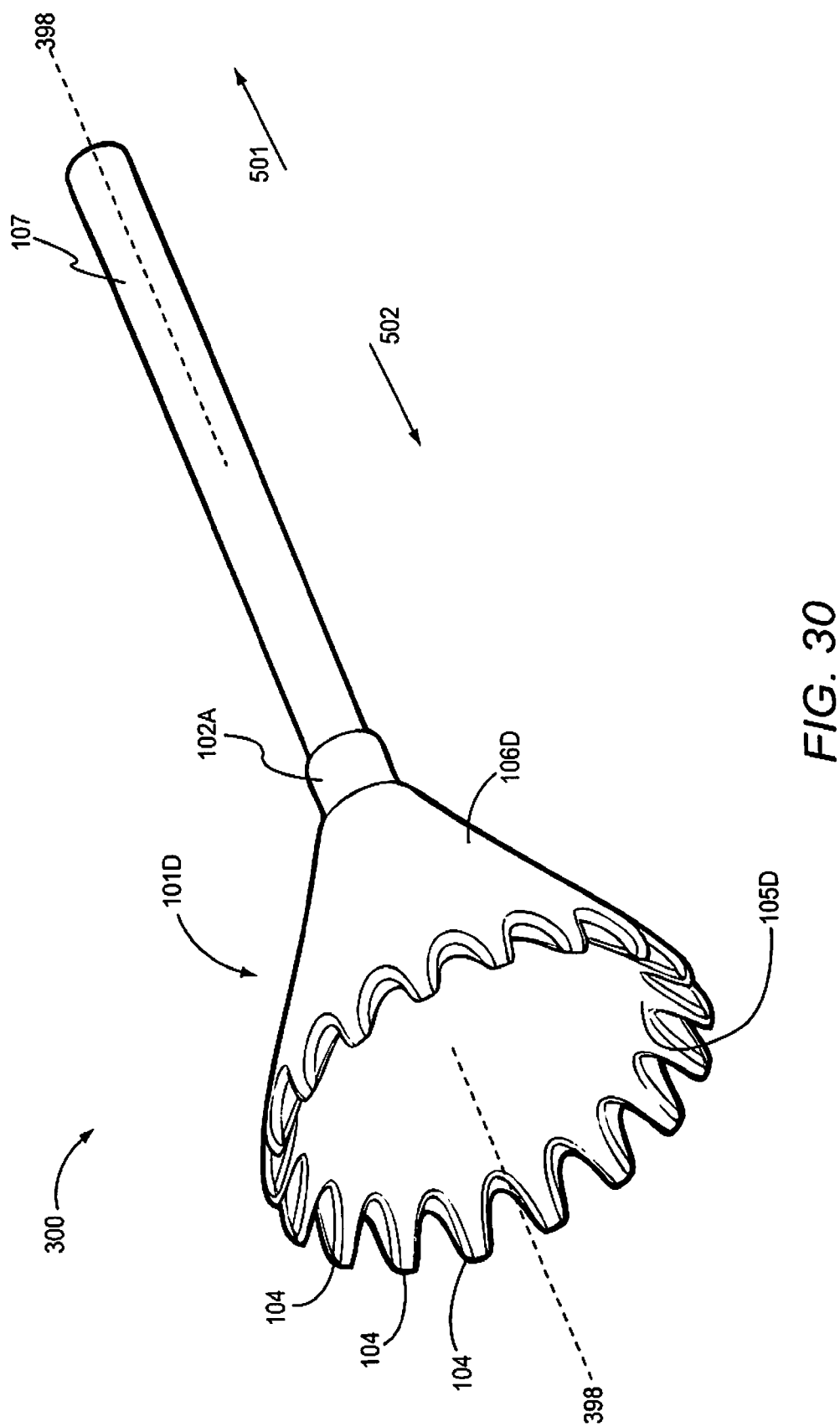
FIG. 30 depicts an oblique, external view of a driveshaft-mounted, rotatable, hollow, flexible, elastic bluntcone, with differentially dissecting projections along its edge, with the axis of rotation of the bluntcone coaxial with the long axis of the drive shaft.

FIG. 30 depicts an oblique, external view of a driveshaft-mounted, hollow, flexible, elastic bluntcone 300, complete with differentially dissecting projections 104 along its edge 103, with the axis of rotation 102 of the bluntcone coaxial with the long axis 398 of the drive shaft 107.

Figure 31:
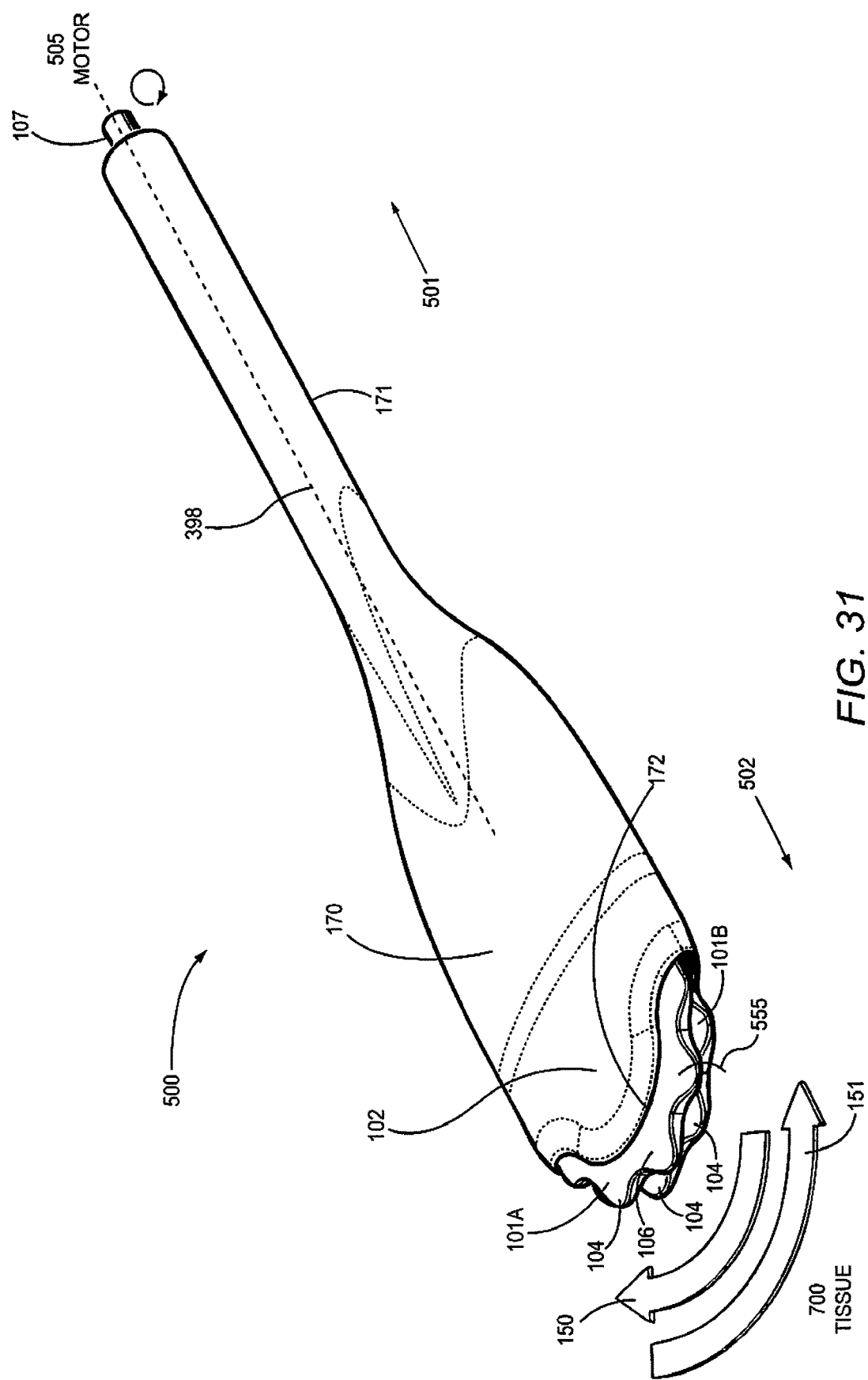
FIG. 31 shows an oblique, external view of one embodiment of the distal portion of a powered differential dissection instrument for achieving safe blunt dissection.

FIG. 31 shows an oblique, external view of one embodiment 500 of the distal portion of a powered differential dissection instrument for achieving safe blunt dissection. In FIG. 31, two counter-rotating, passing edges 555 sporting projections 104 configured for blunt dissection are presented to a complex tissue to be dissected. The projections 104 are configured to differentially dissect a complex tissue on contact when the device is operative. Achieving differential dissection is effected by impinging the two sets 555 of passing projections 104 to the complex tissue to be dissected, regardless of the internal mechanism creating the two sets of passing projections. In one embodiment, the two sets of passing projections can be attained internally by employing twin counter-rotating bluntwheels as shown in FIGS. 1 through 10. In another embodiment, the two sets of passing projections can be attained internally by employing twin counter-rotating bent bluntwheels as depicted in FIGS. 26 through 29. In yet another embodiment, the two sets of passing projections can internally be created by employing one driveshaft-mounted, flexible, folded elastic bluntwheel as shown in FIGS. 11 through 19. In still another embodiment, the two sets of passing projections can be produced by internally using one driveshaft-mounted, hollow, flexible, flattened elastic bluntcones as illustrated in FIGS. 20 through 25.

One normally skilled in the art will appreciate that many variations and combinations of the devices and components herein are possible without violating the spirit of the invention. The many variations and combinations of the devices and components herein are therefore included.

We claim:

1. A differential dissecting instrument for differentially dissecting complex tissue comprising:
   a rotary drive train having a central, longitudinal axis, a distal end, and a proximal end;
   at least one differential dissecting bluntwheel, wherein the at least one differential dissecting bluntwheel:
   is rotatably associated with the distal end of the rotary drive train;
   has an axis of rotation substantially coaxial to the central, longitudinal axis of the rotary drive train; and
   is rotated by the rotary drive train.

2. A differential dissecting instrument as in claim 1, wherein the differential dissecting instrument comprises a plurality of differential dissecting bluntwheels.

3. A differential dissecting instrument as in claim 1, wherein the differential dissecting instrument comprises two differential dissecting bluntwheels.

4. A differential dissecting instrument as in claim 1, wherein the at least one differential dissecting bluntwheel is constructed out of a substantially rigid, high-modulus material.

5. A differential dissecting instrument as in claim 4, wherein a modulus of the at least one differential dissecting bluntwheel is greater than $10^9$ Pascals.

6. A differential dissecting instrument as in claim 3, wherein axes of rotation of the two differential dissecting bluntwheels are concentric.

7. A differential dissecting instrument as in claim 3, wherein axes of rotation of the two differential dissecting bluntwheels are non-parallel.

8. A differential dissecting instrument as in claim 1, wherein the at least one differential dissecting bluntwheel is constructed out of a substantially flexible, low-modulus material.

9. A differential dissecting instrument as in claim 8, wherein a modulus of the at least one differential dissecting bluntwheel is less than $10^6$ Pascals.

10. A differential dissecting instrument as in claim 1, wherein the at least one differential dissecting bluntwheel comprises a wheel or disk having at least one blunt, differentially dissecting, tissue-engaging projection along or forming its edge or margin.

\* \* \* \* \*